US010509044B2

(12) United States Patent
Defilippi et al.

(10) Patent No.: US 10,509,044 B2
(45) Date of Patent: Dec. 17, 2019

(54) METHODS FOR ASSESSING DIFFERENTIAL RISK FOR DEVELOPING HEART FAILURE

(71) Applicants: Christopher Defilippi, Baltimore, MD (US); Stephen Seliger, Columbia, MD (US); James De Lemos, Southlake, TX (US); Robert H. Christenson, Joppa, MD (US)

(72) Inventors: Christopher Defilippi, Baltimore, MD (US); Stephen Seliger, Columbia, MD (US); James De Lemos, Southlake, TX (US); Robert H. Christenson, Joppa, MD (US)

(73) Assignees: UNIVERSITY OF MARYLAND, BALTIMORE, Baltimore, MD (US); BOARD OF REGENT, THE UNIVERSITY OF TEXAS SYSTEM, Austin, TX (US)

(*) Notice: Subject to any disclaimer, the term of this patent is extended or adjusted under 35 U.S.C. 154(b) by 58 days.

(21) Appl. No.: 15/309,754

(22) PCT Filed: May 8, 2015

(86) PCT No.: PCT/US2015/029838
§ 371 (c)(1),
(2) Date: Nov. 8, 2016

(87) PCT Pub. No.: WO2015/171989
PCT Pub. Date: Nov. 12, 2015

(65) Prior Publication Data
US 2017/0234888 A1 Aug. 17, 2017

Related U.S. Application Data

(60) Provisional application No. 61/990,386, filed on May 8, 2014.

(51) Int. Cl.
*G01N 33/68* (2006.01)
*G01N 33/53* (2006.01)

(52) U.S. Cl.
CPC .. *G01N 33/6893* (2013.01); *G01N 2333/4712* (2013.01); *G01N 2333/58* (2013.01); *G01N 2800/32* (2013.01); *G01N 2800/325* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 2002/0128259 | A1* | 9/2002 | Ghazzi | A61K 31/00 514/215 |
|---|---|---|---|---|
| 2012/0164669 | A1 | 6/2012 | Hess | |
| 2014/0065648 | A1 | 3/2014 | Wienhues-Thelen | |
| 2014/0273273 | A1* | 9/2014 | Ballantyne | G01N 33/6887 436/501 |

OTHER PUBLICATIONS

Anderson, Molecular Basis of Human Cardiac Troponin T Isoforms Expressed in the Developing, Adult, and Failing Heart, Circulation Research, 76: 681-686 (1995).
Aurigemma, Predictive Value of Systolic and Diastolic Function for Incident Congestive Heart Failure in the Elderly: The Cardiovascular Health Study, J Am Coll Cardiol, 37: 1042-1048 (2001).
Bonow, New Insights Into the Cardiac Natriuretic Peptides, Circulation 93: 1946-1950 (1996).
Ferrieres, Human cardiac troponin I: precise identification of antigenic epitopes and prediction of secondary structure, Clinical Chemistry, 44: 487-493 (1998).
Borlaug, Diastolic and Systolic Heart Failure are Distinct Phenotypes of the Heart Failure Syndrome, Circulation, 123: 2006-2013 (2011).
Breslow, Covariance Analysis of Censored Survival Data, Biometrics, 30: 89-99 (1974).
Defilippi, Abstract 16937: Initiation of Moderate Physical Activity Reduces Progression of Subclinical Cardiac Injury in Previously Sedentary Older Adults: Results From a Randomized Pilot Study of Exercise Intervention, J Am Coll Cardiol, 55: 441-450 (2010).
Defilippi, Association of Serial Measures of Cardiac Troponin T Using a Sensitive Assay With Incident Heart Failure and Cardiovascular Mortality in Older Adults, JAMA, 304: 2494-2502 (2010).
Defilippi, Abstract 16937: Initiation of Moderate Physical Activity Reduces Progression of Subclinical Cardiac Injury in Previously Sedentary Older Adults: Results From a Randomized Pilot Study of Exercise Intervention, Circulation, 128: 16937 (2013).
Gardin, Sex, Age, and Disease Affect Echocardiographic Left Ventricular Mass and Systolic Function in the Free-Living Elderly, Circulation, 91: 1739-1748 (1995).
De Keulenaer, Are Systolic and Diastolic Heart Failure Overlapping or Distinct Phenotypes Within the Heart Failure Spectrum?, Circulation, 123: 1996-2005 (2011).
Devereux, Echocardiographic Assessmen of Left Ventricular Hypertrophy:Comparison to Necropsy Findings, Am J Cardiol, 57: 450-458 (1986).
Douglas, Appropriate Use Criteria for Echocardiography, J Am Soc Echocardiogr, 24: 229-267 (2011).
Drazner, The Progression of Hypertensive Heart Disease, Circulation, 123: 327-334 (2011).

(Continued)

*Primary Examiner* — Changhwa J Cheu
(74) *Attorney, Agent, or Firm* — Nevrivy Patent Law Group P.L.L.C.

(57) ABSTRACT

The present invention provides a method for predicting whether a human patient 65 years of age or older is at increased risk for developing heart failure, comprising obtaining the results of an assay that measures levels of NT-proBNP and/or cardiac troponin T in a specimen from the patient wherein an increased NT-proBNP and/or cardiac troponin T level compared to levels in a control indicate an increased risk for developing heart failure.

11 Claims, 10 Drawing Sheets

(56) References Cited

OTHER PUBLICATIONS

Drazner, Increased Left Ventricular Mass Is a Risk Factor for the Development of a Depressed Left Ventricular Ejection Fraction Within Five Years, J Am Coll Cardiol, 43: 2207-2215 (2004).
Fried, The Cardiovascular Health Study: Design and Rationale, Ann Epidemiol, 1: 263-276 (1991).
Gonzalez, New Targets to Treat the Structural Remodeling of the Myocardium, J Am Coll Cardiol, 58: 1833-1843 (2011).
Giannitsis, Analytical Validation of a High-Sensitivity Cardiac Troponin T Assay, Clin Chem, 56: 254-261 (2010).
Goas, Heart Disease and Stroke Statistics—2014 Update:, Circulation, 129: 28/2921 (2014).
Glick, Long-term trajectory of two unique cardiac biomarkers and subsequent left ventricular structural pathology and risk of incident heart failure in community dwelling older adults at low baseline risk, JACC Heart Fail, 1: 353-360 (2013).
Ho, Predictors of New-Onset Heart Failure Differences in Preserved Versus Reduced Ejection Fraction, Circ Heart Fail, 6: 279-286 (2013).
Ives, Surveillance and Ascertainment of Cardiovascular Events the Cardiovascular Health Study, Ann Epidemiol, 5: 278-285 (1995).
James, 2014 evidence-based guideline for the management of high blood pressure in adults: Report from the panel members appointed to the eighth joint national committee (JNC 8), JAMA, 311: 507-520 (2013). members.
Karl, Development of a novel, N-Terminal-proBNP (NT-proBNP) assay with a low detection limit, Scand J Clin Invest 59: 177-181 (1999).
Khouri, A 4-Tiered Classification of Left Ventricular Hypertrophy Based on Left Ventricular Geometry the Dallas Heart Study, Circ Cardiovasc Imaging 3: 164-171 (2010).
Kjeldsen, Effects of Losartan on Cardiovascular Morbidity and Mortality in Patients With Isolated Systolic Hypertension and Left Ventricular Hypertrophy, JAMA, 288: 1491-1498 (2002).
Lang, Recommendations for chamber quantification, European Journal of Echocardiography, 7: 79-108 (2006).
Ledwidge, Natriuretic Peptide—Based Screening and Collaborative Care for Heart Failure, JAMA, 310: 66-74 (2013).
Leening, Net Reclassification Improvement: Computation, Interpretation, and Controversies, Ann Intern Med, 160: 122-131 (2004).
Lieb, Longitudinal Tracking of Left Ventricular Mass Over the Adult Life Course, Circulation, 119: 3085-3092 (2009).
Lonn, Effects of Ramipril on Left Ventricular Mass and Function in Cardiovascular Patients With Controlled Blood Pressure and With Preserved Left Ventricular Ejection Fraction, J Am Coll Cardiol, 43: 2200-2206 (2004).
Neeland, Biomarkers of Chronic Cardiac Injury and Hemodynamic Stress Identify a Malignant Phenotype of Left Ventricular Hypertrophy in the General Population, J Am Coll Cardiol, 61: 187-195 (2013).
Owan, Trends in Prevalence and Outcome of Heart Failure with Preserved Ejection Fraction, N Engl J Med, 355: 251-259 (2006).
Olsen, N-terminal brain natriuretic peptide predicted cardiovascular events stronger than high-sensitivity C-reactive protein in hypertension: a LIFE substudy, Journal of hypertension, 24: 1531-1539 (2006).
Paulus, A Novel Paradigm for Heart Failure With Preserved Ejection Fraction, J Am Coll Cardiol, 62: 263-271 (2013).
Pencina, Evaluating the added predictive ability of a new marker: From area under the ROC curve to reclassification and beyond, Stat Med, 27: 157-72 (2008).
Van Heerebeek, Myocardial Structure and Function Differ in Systolic and Diastolic Heart Failure, Circulation, 113: 1966-1973 (2006).
Wolf, Prediction of Left Ventricular Mass from the Electrocardiogram, J Electrocardiol, 24: 121-127 (1991).
Yancy, 2013 ACCF/AHA Guideline for the Management of Heart Failure, Circulation, 128: 240-319 (2013).
Yeo, Multicenter evaluation of the Roche NT-proBNP assay and comparison to the Biosite Triage BNP assay, Clinica Chimica Acta, 338: 107-115 (2003).
European Search Report from European Appl. No. 15789449, dated Sep. 26, 2017.
Nambi, Troponin T and N-Terminal Pro-B-Type Natriuretic Peptide: A Biomarker Approach to Predict Heart Failure Risk-The Atherosclerosis Risk in Communities Study, Clinical Chemistry, 59: 1802-1810 (2013).
Butler, Incident Heart Failure Prediction in the Elderly: The Health ABC Heart Failure Score, Circulation Heart Failure, 1: 125-133 (2008).
Eggers, Value of Cardiac Troponin I Cutoff Concentrations below the 99th Percentile for Clinical Decision-Making, Clinical Chemistry, 55: 85-92 (2009).
Scheven, High-sensitive troponin T and N-terminal pro-B type natriuretic peptide are associated with cardiovascular events despite the cross-sectional association with albuminuria and glomerular filtration rate, European Heart Journal, 33: 2272-2281 (2012).
Defilippi, Physical Activity, Change in Biomarkers of Myocardial Stress and Injury, and Subsequent Heart Failure Risk in Older Adults, Journal of the American College of Cardiology, 60: 2539-2547 (2012).
International Search Report from Appl. No. PCT/US2015/029838, dated Sep. 11, 2015.
European Official Communication from EP Appl. No. 15789449.4, dated Jan. 22, 2019.

* cited by examiner

At time of baseline echocardiogram (1989-90 for main cohort, 1994-95 for supplemental African-American cohort)

METHODS FOR ASSESSING DIFFERENTIAL RISK FOR DEVELOPING HEART FAILURE

CROSS REFERENCE TO RELATED APPLICATIONS

This application claims the benefit of U.S. provisional application No. 61/990,386, filed May 8, 2014, which is incorporated herein by reference in its entirety.

FIELD OF THE INVENTION

The present invention generally relates to the fields of medicine and cardiology. In particular, the invention relates to means and methods for predicting which patients will likely develop a treatable phenotype of heart failure using biomarkers such as cardiac troponin T and a BNP-type peptide such as NT-proBNP.

BACKGROUND OF THE INVENTION

Risk stratification for heart failure in adults involves many clinical challenges. Elderly individuals comprise the largest subgroup of patients hospitalized for heart failure (HF). Once diagnosed with HF, older patients respond less well to guideline-based therapy than their younger counterparts, are more likely to require readmission, and are at higher risk for death.

Blood based biomarkers, including C-reactive protein (CRP), natriuretic peptides, and troponins have been advocated as adjuvants to clinical risk factors to identify community-dwelling older patients at high risk for adverse cardiovascular outcomes, but studies examining the additive prognostic value of these markers have reported inconsistent results. Hypertension is prevalent in greater than 70% of older adults and is commonly associated with left ventricular hypertrophy (LVH). Although LVH is associated with an increased risk of progression to reduced left ventricular systolic function, HF, and death, the progression to a clinical endpoint is heterogeneous occurring in only a small minority. As a result current guidelines don't recommend evaluating "at-risk" populations such as older adults for LVH. There is a need to develop a screen which allows differentiation of which patients with LVH would be at the highest risk for developing progression to heart failure (HF). In particular, identification of patients who are at risk for progression to HF with reduced ejection fraction (HFrEF) would be most advantageous as multiple therapies have been identified to halt the progression of HFrEF, improve symptoms and reduce mortality. Such therapies can also be used in patients with reduced left ventricular ejection fraction (LVEF) who are without symptoms and may have efficacy in LVH to mitigate progression to HF. However, studies of therapeutic effectiveness in LVH have been limited by the relatively low progression to symptoms. Identification of stratification of individuals at risk for new onset HFrEF would have clear advantages as specific therapies can be tested and implemented with high probability of success to reduce progression to symptomatic disease and death.

SUMMARY OF THE INVENTION

It is to be understood that both the foregoing general description of the embodiments and the following detailed description are exemplary, and thus do not restrict the scope of the embodiments.

In one embodiment, the invention provides a method for predicting whether a human patient 65 years of age or older is at increased risk for developing heart failure, comprising obtaining the results of an assay that measures levels of NT-proBNP and/or cardiac troponin T (cTnT) in a specimen from the patient wherein an increased NT-proBNP and/or cardiac troponin T level compared to levels in a control indicate an increased risk for developing heart failure.

In another embodiment, the invention provides a method for predicting whether a human patient 65 years of age or older is at greater risk for developing heart failure, comprising obtaining the results of an assay that monitors levels of NT-proBNP and/or cardiac troponin T in specimens from the patient over time, wherein increasing levels of NT-proBNP and/or cardiac troponin T over time indicate an increased risk for developing heart failure.

In another embodiment, the invention provides a method for treating a human patient 65 years of age or older to prevent advance to a heart failure event comprising
  i) obtaining the results of an assay measuring levels of NT-proBNP and/or cardiac troponin T in a specimen from the patient wherein an increased NT-proBNP and/or cardiac troponin T level compared to levels in a control indicate an increased risk for developing heart failure; and
  ii) administering to the patient an effective amount of one or more ACE inhibitors, angiotensin receptor blockers, beta-blockers, angiotensin receptor neprilysin inhibitors, aldosterone receptor antagonists, life style modification (inclusive of increasing physical activity), specialty consultation with a cardiovascular specialist and combinations thereof.

In another embodiment, the invention provides a method for treating a human patient 65 years of age or older to prevent advance to a heart failure event comprising
  i) obtaining the results of an assay that monitored levels of NT-proBNP and/or cardiac troponin T in specimens from the patient over time, wherein increasing levels of NT-proBNP and/or cardiac troponin T over time indicate an increased risk for developing heart failure; and
  ii) administering to the patient an effective amount of one or more ACE inhibitors, angiotensin receptor blockers, beta-blockers, angiotensin receptor neprilysin inhibitors, aldosterone receptor antagonists, life style modification (inclusive of increasing physical activity), and specialty consultation with a cardiovascular specialist.

In another embodiment, the invention provides a method of screening for drug effectiveness in a subject to prevent advance to a heart failure event comprising
  i) obtaining the results of an assay measuring levels of NT-proBNP and/or cardiac troponin T in a specimen from the subject wherein an increased NT-proBNP and/or cardiac troponin T level compared to levels in a control indicate an increased risk for developing heart failure; and
  ii) administering to the subject an amount of the drug after the assay of step i); and
  iii) obtaining the results of an assay measuring levels of NT-proBNP and/or cardiac troponin T in a specimen from the subject after the administering of step ii), wherein a reduction in NT-proBNP and/or cardiac troponin T in the sample from the subject compared to the NT-proBNP and/or cardiac troponin T in the sample from the subject in step i) indicates that the drug may be effective in preventing advance to a heart failure event.

In another embodiment, the invention provides a method of screening for drug effectiveness in a subject to prevent advance to a heart failure event comprising
   i) obtaining the results of an assay that monitored levels of NT-proBNP and/or cardiac troponin T in specimens from the subject over time, wherein increasing levels of NT-proBNP and/or cardiac troponin T over time indicate an increased risk for developing heart failure; and
   ii) administering to the subject an amount of the drug after the assay of step i); and
   iii) obtaining the results of an assay measuring levels of NT-proBNP and/or cardiac troponin T in a specimen from the subject after the administering of step ii), wherein a reduction in NT-proBNP and/or cardiac troponin T in the sample from the subject compared to the NT-proBNP and/or cardiac troponin T in the sample from the subject in step i) indicates that the drug may be effective in preventing advance to a heart failure event.

In another embodiment, the invention provides a method for distinguishing a probability or risk of HFrEF relative to HFpEF in a human patient 65 years of age or older having LVH comprising obtaining the results of an assay measuring levels of NT-proBNP and/or cardiac troponin T in a specimen from the patient, wherein an increased NT-proBNP and/or cardiac troponin T compared to levels in a control indicate a relative increased probability or risk of HFrEF relative to developing HFpEF in the patient.

In another embodiment, the invention provides a method for distinguishing a probability or risk of HFrEF relative to HFpEF in a human patient 65 years of age or older having LVH comprising obtaining the results of an assay measuring levels of NT-proBNP and/or cardiac troponin T in a specimen(s) from the patient over a period of time, wherein increasing NT-proBNP and/or cardiac troponin T levels over time indicate a relative increased probability or risk of HFrEF relative to developing HFpEF in the patient.

In another embodiment, the invention provides a method for predicting whether a human patient 65 years of age or older is at increased risk for developing heart failure, comprising
   i) obtaining the results of an assay that measures levels of NT-proBNP;
   ii) obtaining the results of an assay that measures levels of cardiac troponin T; and
   iii) obtaining the results of an assay that determines whether the patient has LVH;
   wherein the patient is at increased risk for heart failure if
      a. the level of NT-proBNP is increased relative to a control, the level of cardiac troponin T is increased relative to a control and the patient has LVH;
      b. the level of NT-proBNP is increased relative to a control and the level of cardiac troponin T is increased relative to a control;
      c. the level of NT-proBNP is increased relative to a control and the patient has LVH; or
      d. the level of cardiac troponin T is increased relative to a control and the patient has LVH.

In another embodiment, the invention provides a method for predicting whether a human patient 65 years of age or older is at increased risk for developing heart failure, comprising
   i) obtaining the results of an assay that measures levels of NT-proBNP in specimens from the patient over time;
   ii) obtaining the results of an assay that measures levels of cardiac troponin T in specimens from the patient over time; and
   iii) obtaining the results of an assay that determines whether the patient has LVH;
   wherein the patient is at increased risk for heart failure if
      a. the level of NT-proBNP is increasing over time, the level of cardiac troponin T is increasing over time and the patient has LVH;
      b. the level of NT-proBNP is increasing over time and the level of cardiac troponin T is increasing over time;
      c. the level of NT-proBNP is increasing over time and the patient has LVH; or
      d. the level of cardiac troponin T is increasing over time and the patient has LVH.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1A:
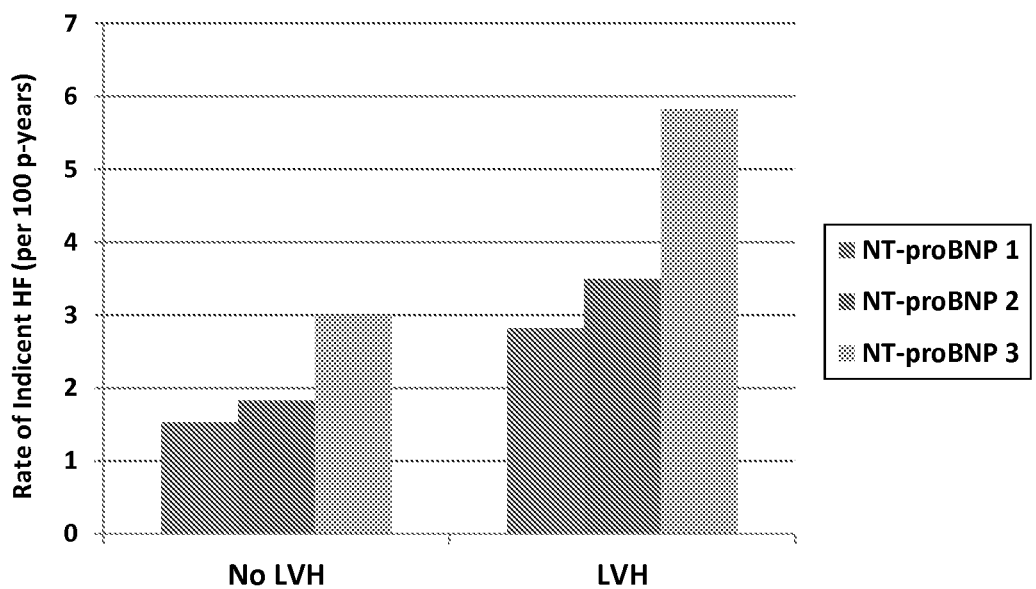
FIG. 1. Rate of incident heart failure, by LVH and tertile of NT-proBNP (a) or hs cTnT (b).

The invention is based on the surprising discovery that heart failure risk in patients 65 years old and older, particularly, heart failure with reduced ejection fraction (HFrEF), can be accurately predicted, even in patients who are asymptomatic. Identifying such patients early and in advance of heart failure provides a unique opportunity to intervene and treat patients at risk to prevent progression to heart failure, particularly heart failure with reduced ejection fraction (HFrEF).

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

In one embodiment, the invention provides a method for predicting whether a human patient 65 years of age or older is at increased risk for developing heart failure, comprising obtaining the results of an assay that measures levels of NT-proBNP and/or cardiac troponin T in a specimen from the patient wherein an increased NT-proBNP and/or cardiac troponin T level compared to levels in a control indicate an increased risk for developing heart failure.

In another embodiment, the invention provides a method for predicting whether a human patient 65 years of age or older is at greater risk for developing heart failure, comprising obtaining the results of an assay that monitors levels of NT-proBNP and/or cardiac troponin T in specimens from the patient over time, wherein increasing levels of NT-proBNP and/or cardiac troponin T over time indicate an increased risk for developing heart failure.

In another embodiment, the invention provides a method for treating a human patient 65 years of age or older to prevent advance to a heart failure event comprising
i) obtaining the results of an assay measuring levels of NT-proBNP and/or cardiac troponin T in a specimen from the patient wherein an increased NT-proBNP and/or cardiac troponin T level compared to levels in a control indicate an increased risk for developing heart failure; and
ii) administering to the patient an effective amount of one or more ACE inhibitors, angiotensin receptor blockers, beta-blockers, angiotensin receptor neprilysin inhibitors, aldosterone receptor antagonists, life style modification (inclusive of increasing physical activity), specialty consultation with a cardiovascular specialist and combinations thereof.

In another embodiment, the invention provides a method for treating a human patient 65 years of age or older to prevent advance to a heart failure event comprising
i) obtaining the results of an assay that monitored levels of NT-proBNP and/or cardiac troponin T in specimens from the patient over time, wherein increasing levels of NT-proBNP and/or cardiac troponin T over time indicate an increased risk for developing heart failure; and
ii) administering to the patient an effective amount of one or more ACE inhibitors, angiotensin receptor blockers, beta-blockers, angiotensin receptor neprilysin inhibitors, aldosterone receptor antagonists, life style modification (inclusive of increasing physical activity), and specialty consultation with a cardiovascular specialist.

In another embodiment, the invention provides a method of screening for drug effectiveness in a subject to prevent advance to a heart failure event comprising
i) obtaining the results of an assay measuring levels of NT-proBNP and/or cardiac troponin T in a specimen from the subject wherein an increased NT-proBNP and/or cardiac troponin T level compared to levels in a control indicate an increased risk for developing heart failure; and
ii) administering to the subject an amount of the drug after the assay of step i); and
iii) obtaining the results of an assay measuring levels of NT-proBNP and/or cardiac troponin T in a specimen from the subject after the administering of step ii), wherein a reduction in NT-proBNP and/or cardiac troponin T in the sample from the subject compared to the NT-proBNP and/or cardiac troponin T in the sample from the subject in step i) indicates that the drug may be effective in preventing advance to a heart failure event.

In another embodiment, the invention provides a method of screening for drug effectiveness in a subject to prevent advance to a heart failure event comprising
i) obtaining the results of an assay that monitored levels of NT-proBNP and/or cardiac troponin T in specimens from the subject over time, wherein increasing levels of NT-proBNP and/or cardiac troponin T over time indicate an increased risk for developing heart failure; and
ii) administering to the subject an amount of the drug after the assay of step i); and
iii) obtaining the results of an assay measuring levels of NT-proBNP and/or cardiac troponin T in a specimen from the subject after the administering of step ii), wherein a reduction in NT-proBNP and/or cardiac troponin T in the sample from the subject compared to the NT-proBNP and/or cardiac troponin T in the sample from the subject in step i) indicates that the drug may be effective in preventing advance to a heart failure event.

In some embodiments, the subject is a mammal selected from the group consisting of humans, primates, monkeys, chimpanzees, dogs, cats, sheep, cattle, goats, pigs, horses, chickens, mice, rats, rabbits, and guinea pigs.

In another embodiment, the invention provides a method for distinguishing a probability or risk of HFrEF relative to HFpEF in a human patient 65 years of age or older having LVH comprising obtaining the results of an assay measuring levels of NT-proBNP and/or cardiac troponin T in a specimen from the patient, wherein an increased NT-proBNP and/or cardiac troponin T compared to levels in a control indicate a relative increased probability or risk of HFrEF relative to developing HFpEF in the patient.

In another embodiment, the invention provides a method for distinguishing a probability or risk of HFrEF relative to HFpEF in a human patient 65 years of age or older having LVH comprising obtaining the results of an assay measuring levels of NT-proBNP and/or cardiac troponin T in a specimen(s) from the patient over a period of time, wherein increasing NT-proBNP and/or cardiac troponin T levels over time indicate a relative increased probability or risk of HFrEF relative to developing HFpEF in the patient.

In another embodiment, the invention provides a method for predicting whether a human patient 65 years of age or older is at increased risk for developing heart failure, comprising
 i) obtaining the results of an assay that measures levels of NT-proBNP;
 ii) obtaining the results of an assay that measures levels of cardiac troponin T; and
 iii) obtaining the results of an assay that determines whether the patient has LVH;
 wherein the patient is at increased risk for heart failure if
  a. the level of NT-proBNP is increased relative to a control, the level of cardiac troponin T is increased relative to a control and the patient has LVH;
  b. the level of NT-proBNP is increased relative to a control and the level of cardiac troponin T is increased relative to a
  c. the level of NT-proBNP is increased relative to a control and the patient has LVH; or
  d. the level of cardiac troponin T is increased relative to a control and the patient has LVH.

In another embodiment, the invention provides a method for predicting whether a human patient 65 years of age or older is at increased risk for developing heart failure, comprising
 i) obtaining the results of an assay that measures levels of NT-proBNP in specimens from the patient over time;
 ii) obtaining the results of an assay that measures levels of cardiac troponin T in specimens from the patient over time; and
 iii) obtaining the results of an assay that determines whether the patient has LVH;
 wherein the patient is at increased risk for heart failure if
  a. the level of NT-proBNP is increasing over time, the level of cardiac troponin T is increasing over time and the patient has LVH;
  b. the level of NT-proBNP is increasing over time and the level of cardiac troponin T is increasing over time;
  c. the level of NT-proBNP is increasing over time and the patient has LVH; or
  d. the level of cardiac troponin T is increasing over time and the patient has LVH.

The methods of the present invention, in some embodiments, are in vitro methods. In some embodiments, the methods can comprise steps in addition to those explicitly mentioned above. For example, further steps may relate to sample pre-treatments or evaluation of the results obtained by the method. The methods of the present invention may be also used for monitoring, confirmation, and subclassification of a subject in need of a cardiac intervention. The method may be carried out manually or assisted by automation. In some embodiments, one or more steps of the methods may in total or in part be assisted by automation, e.g., by a suitable robotic and sensory equipment for any obtaining results steps or a computer-implemented step to compare the levels of the biomarkers or left ventricular mass values to control or reference values.

The term "diagnosing" and "predicting" as used herein mean identifying the risk of progressing to heart failure, on the basis of left ventricular hypertrophy and/or increased levels of one or more of NT-proBNP or cardiac troponin T. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. In some embodiments, confidence intervals are at least 90%, at least 95%, at least 97%, at least 98% or at least 99%. In some embodiments, the p-values can be 0.1, 0.05, 0.01, 0.005, or 0.0001. In some embodiments, at least 60%, at least 70%, at least 80% or at least 90% of the subjects of a population can be properly identified by the method of the present invention.

The term "patient" as used herein refers to a human. The patient referred to in accordance with the aforementioned methods may present with symptoms of heart disease or may be asymptomatic. In some embodiments, the patient is at risk for new onset heart failure. In some embodiments, the patient is at risk for heart failure with reduced ejection fraction (HFrEF). In some embodiments, the patient has not had prior heart failure or myocardial infarction.

Heart disease describes a range of conditions that affect the heart. Diseases under the heart disease umbrella include blood vessel diseases, such as coronary artery disease; heart rhythm problems (arrhythmias); and heart defects that someone is born with (congenital heart defects), among others. The term "heart disease" is often used interchangeably with the term "cardiovascular disease." Cardiovascular disease generally refers to conditions that involve narrowed or blocked blood vessels that can lead to a heart attack, chest pain (angina) or stroke. Other heart conditions, such as those that affect the heart's muscle, valves or rhythm, also are considered forms of heart disease.

"Ejection fraction" refers to a measure of the function of the left ventricle, also called left ventricular ejection fraction (LVEF). The ejection fraction is the percentage of blood ejected from the left ventricle with each heartbeat. The ejection fraction can be measured by a number of techniques, including by ultrasound of the heart (echocardiography), cardiac catheterization, magnetic resonance imaging (MRI) scan of the heart, and nuclear medicine scan (multiple gated acquisition or MUGA) of the heart; also called a nuclear stress test and computerized tomography (CT) scan of the heart. An LVEF of 50% indicates that the left ventricle ejects half its volume each time it contracts.

As used herein, the term "heart failure" encompasses all types of cardiovascular conditions that, regardless of their cause, are generally recognized by a physician as heart failure, which include but are not limited to, acute heart failure, chronic heart failure, and congestive heart failure. Heart failure occurs when the heart is unable to pump sufficiently to maintain blood flow to meet the body's needs. In some embodiments, "heart failure with reduced ejection fraction" (HFrEF) corresponds to an ejection fraction of less than 51% and "heart failure with preserved ejection fraction" (HFpEF) corresponds to an ejection fraction of greater than or equal to 51%. In some embodiments, HFrEF and HFpEF are measured by echocardiogram.

In some embodiments, a patient with HFrEF has an ejection fraction of less than 40%, less than 41%, less than 42%, less than 43%, less than 44%, less than 45%, less than 46%, less than 47%, less than 48%, less than 49%, or less than 50%.

The term "administer" or "administration," as used herein, encompasses various methods of delivering a composition containing a therapeutically effective substance or a treatment to a patient. Modes of administration may include, but are not limited to, methods that involve delivering the composition intravenously, intraperitoneally, intranasally, transdermally, topically, subcutaneously, parentally, intramuscularly, orally, or systemically, and via injection, ingestion, inhalation, implantation, or adsorption by any other means. Some embodiments of intravenous injection include formulating a therapeutically active substance as a sterile solution. Another route of administration is oral ingestion, where the therapeutically active substance can be formulated as a pharmaceutical composition in the form of a syrup, an elixir, a suspension, a powder, a granule, a tablet, a capsule, a lozenge, a troche, and an aqueous solution. In some embodiments, the therapeutically active substance is formulated as a cream, an ointment, a lotion, a gel, or an emulsion. In some embodiments, the pharmaceutical composition for oral ingestion is formulated for sustained release over a period of at least 24 hours. Furthermore, administration of the therapeutically active substance can be achieved by subcutaneous injection of the composition, which can be prepared as a sustained release system comprising microspheres or biodegradable polymers, such that the therapeutically active substance can be released into a patient's body at a controlled rate over a period of time, e.g., at least 24 hours or 48 hours.

An "effective amount" refers to the amount of an active ingredient in a pharmaceutical composition that is sufficient to produce a beneficial or desired effect at a level that is readily detectable by a method commonly used for detection of such an effect. In some embodiments, such an effect results in a change of at least 10% from the value of a basal level where the active ingredient is not administered, more preferably the change is at least 20%, 50%, 80%, or an even higher percentage from the basal level. The effective amount of an active ingredient can vary from subject to subject, depending on age, general condition of the subject, the severity of the condition being treated, and the particular biologically active agent administered, and the like. An appropriate "effective" amount in any individual case may be determined by one of ordinary skill in the art by reference to the pertinent texts and literature and/or by using routine experimentation.

The term "sample" or "specimen" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum.

The term "cardiac troponin" refers to all troponin isoforms expressed in cells of the heart and, preferably, the subendocardial cells. These isoforms, such as cardiac troponin T, are well characterized in the art as described, e.g., in Anderson 1995, *Circulation Research*, vol. 76, no. 4: 681-686 and Ferrieres 1998, *Clinical Chemistry*, 44: 487-493. In some embodiments, cardiac troponin refers to cardiac troponin T. The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

The term "brain natriuretic peptide (BNP)-type peptides" relates to pre-proBNP, proBNP, NT-proBNP, and BNP and variants thereof (see e.g. Bonow, 1996, *Circulation* 93: 1946-1950). Specifically, the aforementioned pre-pro peptide of the brain natriuretic peptide (having 134 amino acids in length) comprises a short signal peptide, which is enzymatically cleaved off to release the pro peptide (108 amino acids). The pro peptide is further cleaved into an N-terminal pro peptide (NT-pro peptide, 76 amino acids) and the active hormone (32 amino acids). BNP is metabolised in the blood, whereas NT-proBNP circulates in the blood as an intact molecule and as such is eliminated renally.

A BNP-type peptide referred to herein is human NT-proBNP. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in published applications, e.g., WO 02/089657 and WO 02/083913. In some embodiments, the human NT-proBNP as used herein is human NT-proBNP as disclosed in EP 0 648 228 B1. These documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e.

epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, *Scand J Clin Invest* 59:177-181), Yeo et al. (Yeo 2003, *Clinica Chimica Acta* 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

Obtaining the results of an assay measuring or monitoring levels of NT-proBNP and/or cardiac troponin T and/or LVH referred to in this specification encompasses measuring the amount or concentration, preferably semi-quantitatively or quantitatively. In some embodiments, the step of obtaining the results of an assay measuring or monitoring levels of NT-proBNP and/or cardiac troponin T and/or LVH can encompass ordering a third party to perform the assay or using the results obtained from a third party without directing the third party to perform the measurements, for example, if the results are already available. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal, sometimes referred to herein as intensity signal, may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the level of a peptide or polypeptide can be achieved by all known methods for determining the amount of a peptide in a sample. Such methods comprise immunoassay devices and methods which may utilize labeled molecules in various sandwich, competition, or other assay formats. Such assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Such methods comprise, in some embodiments, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on ELECSYS analyzers, Roche Diagnostics GmbH), CBA (an enzymatic cobalt binding assay, available for example on Roche-Hitachi analyzers), and latex agglutination assays (available for example on Roche-Hitachi analyzers).

In some embodiments, the levels of cardiac troponin T are measured with a high sensitive (hs) assay (hs cTnT). In some embodiments, the levels of cardiac troponin T and/or NT-proBNP are measured with an antibody-based assay. In some embodiments, NT-proBNP and cTnT are measured using a sandwich immunoassay. In some embodiments, hs cTnT and/or NT-proBNP can be measured on the Elecsys 2010 analyzer (Roche Diagnostics, Indianapolis, Ind.). deFilippi et al. J Am Coll Cardiol. 2010; 55:441-450; deFilippi et al. Jama. 2010; 304:2494-2502; Giannitsis et al. Clin Chem. 2010; 56:254-261. In some embodiments, NT-proBNP and cTnT can be measured on the Cobas e 411. (e 411) analyzer and the Cobas e 601 (e601) module (Roche Diagnostics, Indianapolis, Ind.). The 2010, e601 and e601 measure hs-TnT and NT-proBNP using the principle of sandwich immunoassay and ElectroChemiLuminescence (ECL) technology. The principle for these systems is formation of a 'sandwich' immunoassay complex in which antigen analyte (either TnT or NT-proBNP) is bound by two monoclonal antibodies, each targeting a different epitope location on the antigen analyte molecule. One of the monoclonal antibodies is bound to the substance biotin; the other analyte specific monoclonal antibody to a different epitope location is labeled with a Ruthenium complex for detection. During an initial incubation period, these two monoclonal antibodies are mixed with a sample containing the analyte (TnT or NT-proBNP). Because each antibody has high affinity for a different epitope on the analyte molecule, a <biotinylated antibody-analyte-Ruthenium antibody> sandwich complex is formed during the initial incubation. In a second step, streptavidin coated paramagnetic beads are added to the same measurement cell and incubated, Because streptavidin and biotin form one of the strongest, most resilient non covalent bond in nature, the paramagnetic beads serve to capture the immune complex sandwich containing analyte (TnT or NT-proBNP). The reaction mixture is aspirated into a reaction cell where a magnetic field is applied, which causes the magnetic beads to bind to the surface of the measurement cell. Unbound substances are then removed by treatment with a solution (ProCell/ProCell M). This solution also provides tripropylamide, which is essential for the ECL reaction. Application of a voltage to the electrode induces chemiluminescent emission, which is measured by a photomultiplier tube. The concentration of each analyte (TnT or NT-proBNP) in samples is determined from a calibration curve which is instrument-specifically generated by a two point calibration a master curve provided by the reagent barcode.

The term "comparing" as used herein encompasses comparing the amount of the polypeptide within the specimen to be analyzed or the left ventricular mass index with an amount of a suitable reference or control source. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. A comparison referred to in the methods of the present invention can be carried out manually or computer assisted. For a computer assisted comparison, the value of the determined amount can be compared to values corresponding to suitable references which are stored in a database by a computer program. The computer program may further evaluate the result of the comparison, i.e. automatically provide the desired assessment in a suitable output format. Based on the comparison of the levels of NT-proBNP and/or cardiac troponin T and/or left ventricular mass index with the reference amount(s), it is possible to predict whether the patient is at risk for heart failure, particularly HFrEF. Therefore, in some embodiments, the reference amount is to be chosen so that either a difference or a similarity in the compared amounts allows identifying those subjects which belong into the group of subjects at risk for heart failure.

In some embodiments, the reference or control source comprises values from age and/or gender matched controls. In some embodiments, the reference or control source can comprise values according to race/ethnicity, diabetic status, whether coronary heart disease is present or absent, body mass index, blood pressure (systolic and/or diastolic), smoking status or a combination thereof.

In some embodiments, the levels of NT-proBNP and/or cardiac troponin T in specimens from the patient are monitored over time, wherein increasing levels of NT-proBNP and/or cardiac troponin T over time indicate an increased risk for developing heart failure, particularly HFrEF. Accordingly, in some embodiments, the "reference amount" or control amount is an amount of the biomarker assayed from the same patient from one or more earlier points in time. In some embodiments, the levels of levels of NT-proBNP and/or cardiac troponin T are measured about every 3 months, 4 months, 5 months, 6 months, 7 months, 8 months, 9 months, 10 months, 11 months, 12 months, 15 months, 18 months, 1 year, 2 years, 3 years, 4 years, or 5 years. In some embodiments, the levels of NT-proBNP and/or cardiac troponin T are measured over a 1, 2, 3, 4, 5, 6, 7, 8, 9, or 10 year period. In some embodiments, a baseline measurement is taken followed up by a measurement 2 or 3 years later and then compared with the baseline measurement. In some embodiments, the method comprises detecting an increase in NT-proBNP>10% from baseline, >15% from baseline, >20% from baseline, >25% from baseline, >30% from baseline, >35% from baseline, >40% from baseline, >45% from baseline, or 50% from baseline. In some embodiments, the method comprises detecting an increase in cardiac troponin T>25% from baseline, >30% from baseline, >35% from baseline, >40% from baseline, >45% from baseline, >50% from baseline, >55% from baseline, >60% from baseline, 65% from baseline, 75% from baseline or 75% from baseline.

In some embodiments, the method comprises detecting an increase in NT-proBNP from baseline to a final concentration of >85 pg/ml, >90 pg/ml, >95 pg/ml, >100 pg/ml, >105 pg/ml, >110 pg/ml, >115 pg/ml, >120 pg/ml, >125 pg/ml, >130 pg/ml, >135 pg/ml, ≥140 pg/ml, >145 pg/ml, >150 pg/ml, >155 pg/ml, >160 pg/ml, >165 pg/ml, >170 pg/ml, >175 pg/ml, >180 pg/ml, >185 pg/ml, >190 pg/ml, >195 pg/ml, >200 pg/ml, or >205 pg/ml.

In some embodiments, the method comprises detecting an increase in cardiac troponin T from baseline to a final concentration of >3 pg/ml, >3.5 pg/ml, >4 pg/ml, >4.5 pg/ml, >5 pg/ml, >5.5 pg/ml, >6 pg/ml, >6.5 pg/ml, >7 pg/ml, >7.5 pg/ml, >8 pg/ml, ≥8.5 pg/ml, >9 pg/ml, >9.5 pg/ml, >10 pg/ml, >10.5 pg/ml, >11 pg/ml, >11.5 pg/ml, >12 pg/ml, >12.5 pg/ml, >13 pg/ml, >13.5 pg/ml, >14 pg/ml, >14.5 pg/ml, >15 pg/ml, >15.5 pg/ml, >16 pg/ml or >16.5 pg/ml.

In some embodiments, the method comprises detecting an increase in NT-proBNP>25% from baseline to a final concentration of ≥190 pg/ml and/or an increase in cardiac troponin T>50% from baseline.

In some embodiments, the reference amounts or control can be derived from subjects known to suffer from heart failure and from healthy controls that did not previously suffer heart failure. In some embodiments the amounts define thresholds or cut-points. Suitable threshold amounts can be determined from a reference sample to be analyzed together, i.e. simultaneously or subsequently, with the test sample. In some embodiments, a reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques. A suitable technique may be to determine the median of the population for the peptide or polypeptide amounts to be determined in the method of the present invention. In some embodiments, the threshold for cardiac troponin T can vary between 0.001 ng/ml and 0.01 ng/ml. In some embodiments, the threshold for NT-proBNP referred to herein can vary between 90 and 350 pg/ml. In some embodiments, if a patient has a cardiac troponin T value below the limit of blank for the assay, a value of 0.01 ng/L below the limit of blank is imputed as the baseline value.

In some embodiments, the method comprises obtaining the results of a measurement of levels of NT-proBNP and/or cardiac troponin T in a specimen from the patient on one occasion and determining which subjects have values in the upper tertile (upper third) for their age and gender strata, which can indicate a risk for future heart failure.

In some embodiments, the levels of NT-proBNP and/or cardiac troponin T are compared to age and gender matched controls, such that measurements above the following cut-points indicate an increased risk for heart failure:

| Age (years) | Men | Women |
| --- | --- | --- |
| | NT-proBNP (pg/mL) | |
| 65-69 | 93.2 | 122.4 |
| 70-74 | 130.5 | 147.7 |
| 75-79 | 152.8 | 246.3 |
| 80+ | 304.9 | 341.2 |
| | hs-cTnT (pg/mL) | |
| 65-69 | 7.54 | 6.06 |
| 70-74 | 9.23 | 6.00 |
| 75-79 | 10.84 | 7.83 |
| 80+ | 16.61 | 11.07 |

In some embodiments, the cut-points vary by ±20% from the above described cut-points for hs cTnT. In some embodiments, the cut-points vary by ±10% from the above described cut-points for NT-proBNP.

In some embodiments, the patient has left ventricular hypertrophy (LVH) and the presence of LVH in combination with an increased NT-proBNP and/or cardiac troponin T level compared to a control or increasing NT-proBNP and/or cardiac troponin T levels over time indicate an increased risk for developing heart failure.

In some embodiments, the LVH is determined by a method selected from the group consisting of echocardiography, magnetic resonance imaging and electrocardiography. In some embodiments, the determination of LVH can be made with validated definitions of LVH based on cardiac MRI and echocardiography.

In some embodiments, the patient has LVH if the ratio of the measured left ventricular mass (LV) to the expected LV mass is >1.45.

In some embodiments, to determine cut-points for determining LVH by echocardiography, the following can be performed. The expected LV mass based on previously published normative equations derived from the Cardiovascular Health Study (*Circulation* 1995; 91:1739-1748) is determined:

For women: Expected LV mass=$13.9*Weight^{0.51}$
For men: Expected LV mass=$16.6*Weight^{0.51}$
Where weight is in kilograms and LV mass is in grams.
The measured LV mass from echocardiography is compared to expected LV Mass, and if the ratio of measured/expected is >1.45, then the patient is considered to have left ventricular hypertrophy (LVH). That is, LVH is defined if the measured LV mass is more than 45% greater than what would be expected based on gender and body mass.

In some embodiments LV mass can be determined by an electrocardiogram (ECG). In some embodiments, the patient is at increased risk for heart failure if the left ventricular mass index (g/m$^2$) as measured by electrocardiogram is greater than the following cut points for gender matched controls:

| ECG - Left Ventricular Mass Index (g/m$^2$) | |
| --- | --- |
| Men | Women |
| 102.7 | 88.7 |

In some embodiments, the cut points for left ventricular mass index vary by ±10% from the values above.

In some embodiments, LV mass by ECG can be determined as follows: Methods for determining LV mass by electrocardiography: First, a 12-lead surface ECG is recorded according to standard methods for electrode placement. LV mass is estimated with gender- and race-specific equations from the Novacode program, widely used in epidemiologic studies and clinical trials (*J Electrocardiol.* 1991; 24:121-127)
White and black men: LVM=−58.51+0.060*QS(III)+0.021*R($V_5$)−0.033*QS($V_1$)−0.296*Tp(aVR)+0.316*Tn($V_6$)+1.821*QRS.
White women: LVM=134.77+0.023*R($V_5$)−0.155*QS(I)+0.070*QS($V_5$)+0.112*Tp($V_1$)−0.123*Tp($V_6$)+0.032*R(aVL).
Black women: LVM=−90.71+0.050*R(I)−0.051*R($V_1$)−0.098*QS($V_6$)+0.522*Tn(I)+1.848*QRS+0.023*[R($V_6$)+QS($V_2$)].

In some embodiments, the patient at risk for heart failure is administered a treatment to reduce the risk of heart failure. The treatment can include one or more therapeutics and/or can also include lifestyle modification, such as increasing physical activity. In some embodiments, the patient at risk is referred to a cardiovascular specialist for further consultation. In some embodiments, the therapeutics can include one or more angiotensin-converting enzyme (ACE) inhibitors, angiotensin receptor blockers, beta-blockers, angiotensin receptor neprilysin inhibitors, aldosterone receptor antagonists and combinations thereof.

Commonly used ACE inhibitors include ramipril, enalapril, lisinopril, benazepril, enalaprilat, fosinopril, quinapril, moexipril, trandolapril and captopril. In some embodiments, ramipril is administered in a dose from about 1.25 mg to about 20 mg. In some embodiments, enalapril is administered in a dose from about 2.5 mg to about 20 mg. In some embodiments, captopril is administered in a dose from about 6.25 mg to about 150 mg. In some embodiments, enalaprilat is administered in a dose from about 0.625 mg to about 5 mg. In some embodiments, lisinopril is administered in a dose from about 2.5 mg to about 80 mg. In some embodiments, fosinopril is administered in a dose from about 10 mg to about 80 mg. In some embodiments, quinapril is administered in a dose from about 2.5 mg to about 80 mg. In some embodiments, moexipril is administered in a dose from about 3.75 mg to about 60 mg. In some embodiments, trandolapril is administered in a dose from about 1 mg to about 8 mg.

Commonly used angiotensin receptor blockers include azilsartan, candesartan, eprosartan, irbesartan, losartan, olmesartan, telmisartan and valsartan. In some embodiments, azilsartan is administered in a dose of up to about 80 mg. In some embodiments, candesartan is administered in a dose of from about 4 to about 32 mg. In some embodiments, eprosartan is administered in a dose of from about 200 to about 800 mg. In some embodiments, irbesartan is administered in a dose of from about 75 to about 300 mg. In some embodiments, losartan is administered in a dose of from about 12.5 to about 100 mg. In some embodiments, olmesartan is administered in a dose of from about 5 mg to about 40 mg. In some embodiments, telmisartan is administered in a dose of from about 20 mg to about 80 mg. In some embodiments, valsartan is administered in a dose of from about 40 mg to about 80 mg.

Commonly used beta-blockers include carvedilol, metoprolol and metoprolol extended release. In some embodiments, carvedilol is administered in a dose of from about 6.25 to about 50 mg. In some embodiments, metoprolol is administered in a dose of from about 50 to about 450 mg.

Commonly used aldosterone receptor antagonists include spironolactone and eplerenone. In some embodiments, spironolactone is administered in a dose of from about 25 to about 400 mg. In some embodiments, eplerenone is administered in a dose of from about 50 to about 400 mg.

In some embodiments, the angiotensin receptor neprilysin inhibitor is a valsartan/sacubitril combination (LCZ696). LCZ696 is co-crystallized valsartan and sacubitril, in a one-to-one molar ratio. In some embodiments, LCZ696 is administered in a dose of from about 200 to about 400 mg.

In another embodiment, the present invention relates to a method for predicting which patients are at greatest risk for developing new onset HF, particularly HFrEF, comprising measuring rising levels of NT-proBNP and, or cardiac troponin T measured with a high sensitive (hs) assay such as an antibody based assay, collected from the patients serum over time, e.g. 2-3 year time period.

In another embodiment, the present invention relates to a method for predicting which asymptomatic patients without known HF with left ventricular hypertrophy (LVH) are at higher risk for developing HF, particularly HFrEF, comprising monitoring of levels of NT-proBNP or cardiac troponin T measured with a hs assay in patient specimen(s) collected over time, e.g. a 2-3 year time period.

In another embodiment, the present invention relates to a method for predicting which asymptomatic patients with left ventricular hypertrophy (LVH) but without HF, but are at higher risk for developing HF comprising measuring an increase in NT-proBNP>25% to a final concentration of ≥190 pg/ml or an increase in cardiac troponin T>50% from baseline using a hs assay and imputing a value just below or 0.01 ng/L below the limit of blank.

In another embodiment, the present invention relates to a method for predicting which patients with LVH will progress to HFrEF by monitoring an increase in levels of NT-proBNP or cardiac troponin T over time, e.g. 2-3 year period.

In another embodiment, the present invention relates to a method for predicting which patients with LVH will progress to HFrEF by monitoring NT-proBNP and observing a >25% increase to a final concentration of ≥190 pg/ml or an increase in cardiac troponin T>50% from baseline. For subjects with cardiac troponin T values below the limit of blank for the assay, a value of 0.01 ng/L below the limit of blank is imputed as the baseline value.

In another embodiment, the present invention relates to a method for predicting which patients with LVH will progress to HFrEF comprising measuring NT-proBNP and hs cardiac troponin T on one occasion and determining which subjects have values in the upper tertile (upper third) for their age and gender strata.

In another embodiment, the present invention relates to a method for predicting which patients with LVH will progress to HFrEF by monitoring an increase in levels of NT-proBNP or cardiac troponin T over time, e.g. 2-3 years, and then performing echocardiography in those with rising values.

In another embodiment, the present invention relates to a method for predicting which patients with LVH will progress to HFrEF by monitoring NT-proBNP and cardiac troponin T once and determining which subjects have elevated risk.

In another embodiment, the present invention relates to a method for predicting which patients older than 65 years with LVH will progress to HFrEF by monitoring an increase in levels of NT-proBNP or cardiac troponin T or both over time, e.g. a 1, 2, 3, 4, 5, 6, 7, 8, 9, or 10 year time period.

In another embodiment, the present invention relates to a method for predicting which patients older than 65 years with LVH will progress to HFrEF comprising measuring NT-proBNP and hs cTnT once and determining which subjects have values in the upper tertile (upper third) for their age and gender strata.

In another embodiment, the present invention relates to a method for predicting which patients with LVH will progress to a HF event comprising measuring an increase in NT-proBNP>25% to a final concentration of ≥190 pg/ml or an increase in hs cardiac troponin T>50% from baseline and wherein the HF event is characterized as HFpEF (LVEF≥45%) or HFrEF (LVEF<45%) based on clinical echocardiograms or other cardiac imaging studies performed. For subjects with cardiac troponin T values below the limit of blank for the assay, a value of 0.01 ng/L below the limit of blank is imputed as the baseline value.

In another embodiment, the present invention relates to a method for determining which patients with LVH will progress to HFrEF instead of HFpEF comprising measuring an increase in NT-proBNP>25% to a final concentration of ≥190 pg/ml or an increase in hs cTnT>50% from baseline. For subjects with cardiac troponin T values below the limit of blank for the assay, a value of 0.01 ng/L below the limit of blank is imputed as the baseline value.

In another embodiment, the present invention relates to a method for predicting which patients with LVH will progress to HF comprising measuring NT-proBNP and hs cTnT once and determining which subjects have values in the upper tertile (upper third) for their age and gender strata wherein the HF event is characterized as HFpEF (LVEF≥45%) or HFrEF (LVEF<45%) based on clinical echocardiograms or other cardiac imaging studies performed within a short time In another embodiment, the present invention relates to a method for referral for treating a patient with LVH to prevent advanced to a HF event [HFrEF] determined by monitoring an increase in NT-proBNP>25% to a final concentration of ≥190 pg/ml or an increase in hs cardiac troponin T>50% from baseline wherein the treating comprising administering to the patient ACE inhibitors, angiotensin receptor blockers, beta-blockers, life style modification (inclusive of increasing physical activity), and specialty consultation with a cardiovascular specialist.

In another embodiment, the present invention is a method for diagnosing the risk of progressing from left ventricular dysfunction to HF with a reduced ejection fraction in a human subject, the method comprising i) contacting in vitro a portion of a blood sample from a patient with a ligand comprising specific binding affinity for the cardiac troponin T isoform (cTnT), ii) contacting in vitro a portion of the blood sample from the subject with a ligand comprising specific binding affinity for NT-proBNP, iii) calculating an amount of the cTnT (using a high sensitive assay such as an antibody) and an amount of NT-proBNP based on said steps of contacting, and iv) providing a diagnosis of increased risk of progressing to heart failure with a reduced ejection fraction if the concentration of cTnT is greater than or equal to age- and gender-specific cut points or the concentration of NT-proBNP is greater than or equal to age- and gender-specific cut-points as defined below:

| | hs-cTnT (pg/mL) | | NT-proBNP (pg/mL) | |
| --- | --- | --- | --- | --- |
| Age | Male | Female | Male | Female |
| 65-69 | 7.54 | 6.06 | 93.2 | 122.4 |
| 70-74 | 9.23 | 6.00 | 130.5 | 147.7 |
| 75-70 | 10.84 | 7.83 | 152.8 | 246.3 |
| 80 or older | 16.61 | 11.07 | 304.9 | 341.2 |

In some embodiments, the cut-points vary by ±20% from the above described cut-points for hs cTnT. In some embodiments, the cut-points vary by ±10% from the above described cut-points for NT-proBNP.

While the embodiments have been described with reference to certain particular examples and embodiments herein, those skilled in the art will appreciate that various examples and embodiments can be combined for the purpose of complying with all relevant patent laws (e.g., methods described in specific examples can be used to describe particular aspects of the embodiments and its operation even though such are not explicitly set forth in reference thereto).

Aspects of the present teachings may be further understood in light of the following examples, which should not be construed as limiting the scope of the present teachings in any way.

EXAMPLES

Example 1

Older Adults, "Malignant" Left Ventricular Hypertrophy and Associated Cardiac Specific Biomarker Phenotypes to Identify the Differential Risk of New-onset Reduced Versus Preserved Ejection Fraction Bean Failure—the Cardiovascular Health Study We hypothesized that biomarkers of myocardial injury (hs cTnT) and stress (NT-proBNP) would differentiate HF risk among older adults with LVH. Biomarkers were measured at baseline and after 2-3 years in 2,347 older adults without prior HF in the CHS. LVH and LVEF were determined by echocardiography. Adjusted risk of HF was 3.8-fold higher among those with LVH and highest biomarker tertile, compared with low biomarker levels without LVH, with greater excess risk for HFrEF. Those with LVH and increases in either biomarker were ~3-fold more likely to develop HF— primarily HFrEF. These biomarkers may suggest modifiable targets for prevention.

Background: The natural history of left ventricular hypertrophy (LVH)—an important risk factor for heart failure (HF)—is heterogeneous. We hypothesized that biomarkers of subclinical myocardial injury (high sensitive cardiac troponin T [hs cTnT]) and hemodynamic stress (NT-proBNP) would differentiate HF risk among older adults with LVH.

Methods: NT-proBNP and hs cTnT were measured at baseline and after 2-3 years in older adults without prior HF or MI in the Cardiovascular Health Study. LVH and LV ejection fraction (EF) were determined by echocardiography. HF events were adjudicated over a median 13.1 years and classified as preserved or reduced LVEF (HFpEF or HFrEF). Adjusted risk of HF by LVH and biomarker tertiles, and by LVH and longitudinal increase in each biomarker, was estimated using Cox regression.

Results: Prevalence of LVH was 12.5% among 2,347 participants with complete measures. Adjusted risk of HF (N=643 events) was roughly 3.8-fold higher among participants with LVH and in the highest biomarker tertile, compared to those with low biomarker levels without LVH (NT-proBNP: HR=3.78 [95% CI: 2.78, 5.15]; hs-cTnT: HR=3.86 [2.84, 5.26]). The adjusted risk of HFrEF was 7.8 times higher among those with the highest tertile of hs cTnT and LVH (HR=7.83 [4.43, 13.83]). Those with LVH and longitudinal increases in hs cTnT or NT-proBNP were roughly 3-fold more likely to develop HF—primarily HFrEF—compared to those without LVH and with stable biomarkers Conclusions: The combination of LVH with greater hs cTnT or NT-proBNP levels, and their longitudinal increase, identifies older adults at highest risk for symptomatic HF, especially HFrEF. These biomarkers may characterize subphenotypes in the transition from LVH to HF and suggest modifiable targets for prevention.

Hypertension is present in greater than 70% of older adults, and is commonly associated with LVH. Go A S et al. Circulation. 2014; 129:e28-e2921 Lieb et al. Circulation. 2009; 119:3085-3092. Although LVH is associated with an increased risk of progression to depressed left ventricular systolic function, HF, and death, the progression to a clinical endpoint is heterogeneous, occurring in only a minority. Drazner M H. Circulation. 2011; 123:327-334; Drazner et al. J Am Coll Cardiol. 2004; 43:2207-2215; Kjeldsen et al. Jama. 2002; 288:1491-1498. In a prior study of middle age adults, we showed that biochemical evidence of myocardial injury (as measured by the hs cTnT assay) or myocardial hemodynamic stress (as measured by NT-proBNP) identified a "malignant" phenotype of LVH more likely to progress to heart failure or death. Neeland et al. J Am Coll Cardiol. 2013; 61:187-195. Currently, routine cardiac imaging to screen for LVH in hypertensive patients is not recommended, and several important questions remain before considering hs cTnT or NT-proBNP as part of a strategy to identify individuals with LVH at high risk for progression to HF. Douglas et al. J Am Soc Echocardiogr. 2011; 24:229-267. First, HF is heterogeneous with a near equivalent incidence of HFpEF and HFrEF. Owan et al. N Engl J Med. 2006; 355:251-259. Identification of those at highest risk of HFrEF may be particularly advantageous, as specific therapies exist to reduce progression to symptomatic disease. Yancy et al. Circulation. 2013; 128:e240-319. However, clinical and echocardiographic characteristics still have a limited ability to differentiate who will progress to HFrEF versus HFpEF. De Keulenaer et al. Circulation. 2011; 123:1996-2005; Ho et al. Circ Heart Fail. 2013; 6:279-286. Our prior study in middle-aged adults was not able to examine this heterogeneity in HF outcomes, nor whether longitudinal changes in cardiac biomarkers may further modify the risk associated with LVH. The primary objectives of this study were to: 1) Determine if our prior findings in middle-age adults with LVH would be applicable to older adults, and whether there were differential associations with HFrEF vs. HFpEF. Older adults have a markedly higher incidence of HF—especially HFpEF—compared to younger adults, but also greater comorbidities which can confound the interpretation of cardiac-specific biomarkers; and 2) determine whether longitudinal changes in NT-proBNP and/or hs cTnT in those with LVH are associated with the preferential development of HFrEF rather than HFpEF.

Abbreviations:
hs cTnT: high-sensitivity cardiac troponin T
NT-proBNP amino-terminal pro-B-type natriuretic peptide
LVH Left Ventricular Hypertrophy
HF Heart Failure
HFrEF Heart Failure with reduced Ejection Fraction
HFpEF Heart Failure with preserved Ejection Fraction
CHS Cardiovascular Health Study
LVM Left Ventricular Mass
LVMI Left Ventricular Mass Index
RWT Relative Wall thickness Methods Study Participants The CHS is a prospective observational study of cardiovascular risk factors in older adults. Detailed descriptions of the methods have been described. Fried et al. Ann Epidemiol. 1991; 1:263-276. Study participants included community-dwelling adults ≥65 years enrolled at 4 participating centers. Participants (N=5201) initially enrolled in 1989-90, and an African-American supplemental cohort (N=687) enrolled in 1992-93. For the present analysis, we excluded participants with a prior history of HF, myocardial infarction, or estimated GFR<30 cc/min/1.73 m$^2$ at the time of the initial echocardiogram (see below).

The CHS was approved by the IRBs of the University of Washington and participating centers. All participants gave written informed consent. The present analysis was approved by the IRB of the University of Maryland.

Echocardiography

The methods for echocardiographic assessment have been published previously. Gardin et al. Circulation. 1995; 91:1739-1748. Briefly, two dimensional echocardiography was performed in 1989-90 (main cohort only) and again among both cohorts in 1994-1995. M-Mode measurement of LVM was performed using the method described in Devereux et al. Am J Cardiol. 1986; 57:450-458. LVM could not be estimated in approximately 34% of the main cohort, who were more likely to be older, Caucasian, male, of greater height and weight, and to have hypertension, diabetes, and coronary disease. Gardin et al. Circulation. 1995; 91:1739-1748. Expected LVM was calculated based on normative equations from CHS participants with neither clinical heart disease nor hypertension; left ventricular hypertrophy was defined as an observed/expected LVM>1.45. (12,14) LVMI was calculated as LVM divided by body surface area. For analyses of baseline biomarkers, LVM measured at baseline (main cohort) or 1994-95 (supplemental cohort) was used as the primary predictor variable; for analyses of change in biomarkers, LV mass measured in 1994-95 in both cohorts was used. LVEF was defined as abnormal if visually interpreted as <45%. RWT was computed as previously described as (2*Posterior wall thickness)/(End-diastolic LV diameter). Lang et al. European Journal of Echocardiography. 2006; 7:79-108. Eccentric LVH was defined as LVH with RWT≤0.42, and concentric LVH with RWT>0.42. Lang et al. European Journal of Echocardiography. 2006; 7:79-108.

Biomarker Measurement

NT-proBNP and hs cTnT were measured in serum samples collected at baseline and again after 3 years (main cohort) or 2 years (supplemental cohort) and stored at −70° C. to −80° C. NT-proBNP and cTnT were measured on the Elecsys 2010 analyzer (Roche Diagnostics, Indianapolis, Ind.), as previously reported. deFilippi et al. J Am Coll Cardiol. 2010; 55:441-450; deFilippi et al. Jama. 2010; 304:2494-2502. The performance characteristics of both assays have been described previously. Giannitsis et al. Clin Chem. 2010; 56:254-261.

Primary Outcome

The primary outcome was incident HF, ascertained by participant interview at semiannual study visits, medical record review and examination of Medicare claims data and confirmed by expert adjudication panel as described previously. Ives et al. Ann Epidemiol. 1995; 5:278-285. A HF event was confirmed if a physician diagnosis was present along with documentation in the medical record of a constellation of symptoms and physical signs, supporting clinical findings, or a medical therapy for HF. Events were characterized as HFpEF (LVEF≥45%) or HFrEF (LVEF<45%) based on clinical echocardiograms or other cardiac imaging performed within 30 days of the HF event. Aurigemma et al. *J Am Coll Cardiol.* 2001; 37:1042-1048.

Statistical Analyses

Participants were divided into age- and sex-specific tertiles of each biomarker, and differences across these tertiles were compared separately for those with and without LVH, using ANOVA for continuous variables and Cuzik's Score test for binary variables. 895 (38%) of participants had undetectable hs cTnT below level of blank (<3 ng/L) and were all placed in the first tertile with an imputed value of 2.99 ng/L. Cumulative rates of HF among subjects stratified by LVH and biomarker categories were compared with the log-rank test. Cox proportional hazards models were used to estimate the joint association of LVH and biomarker levels with incident heart failure, adjusting for potential confounding factors selected a priori, as defined in Tables 2 & 3, below. The method of Breslow was used to handle tied events. Breslow N. Biometrics 1974; 30:89-99. Joint associations were estimated using LVH*biomarker interaction terms in adjusted models. Similar analyses were performed using LVMI categories in place of LVH. We estimated improvements in reclassification and discrimination of 10-year HF risk among those with LVH from the addition of each biomarker measurement to traditional risk factors with the net reclassification improvement (NRI) and integrated discrimination improvement (IDI) statistics. Pencina et al. Stat Med 2008; 27:157-72. Consistent with recent recommendations, we used the category-less form of the NRI, as there are no consensus thresholds for classifying HF risk among those with LVH. Leening et al. Ann Intern Med 2014; 160:122-131. Bootstrapping was used to estimate 95% confidence intervals of each NRI.

To examine the joint association of LVH and change in biomarkers with incident HF, Cox proportional hazards models were used, with follow-up time defined as time from the $2^{nd}$ echocardiogram (1994-95). A significant change in biomarkers was defined as: a) an increase in NT-proBNP of >25% to a final level ≥190 pg/mL, or b) an increase in hs cTnT of >50% from baseline. For those participants with an initial hs cTnT below level of blank, a level of 2.99 ng/L was imputed. Changes of this magnitude for cTnT and NT-proBNP have been associated with marked increases in risk of incident HF and cardiovascular death in CHS. deFilippi et al. J Am Coll Cardiol. 2010; 55:441-450; deFilippi et al. Jama. 2010; 304:2494-2502. Adjustments were made for baseline biomarker levels and the same confounding factors as described above, measured at the time of the $2^{nd}$ echocardiogram (except for eGFR, which was measured at the 1992-93 visit). LVH*biomarker change interaction was tested in multivariate models using the likelihood ratio test. Similar analyses were performed using LVMI categories in place of LVH.

Survival analyses were performed for all incident HF, and separately for incident HFrEF and HFpEF. At-risk time was defined as time from the echocardiogram to incident HF, with censoring on death or last observed follow-up; for analyses of HF subtype, participants were additionally censored at time of HF of any other subtype. In sensitivity analyses, we used the Fine-Gray method to model the competing risk of LVH and each biomarker with all-cause mortality. All statistical analyses were performed with Stata/SE 12.1 (College Station, Tex.).

Results

Figure 4:
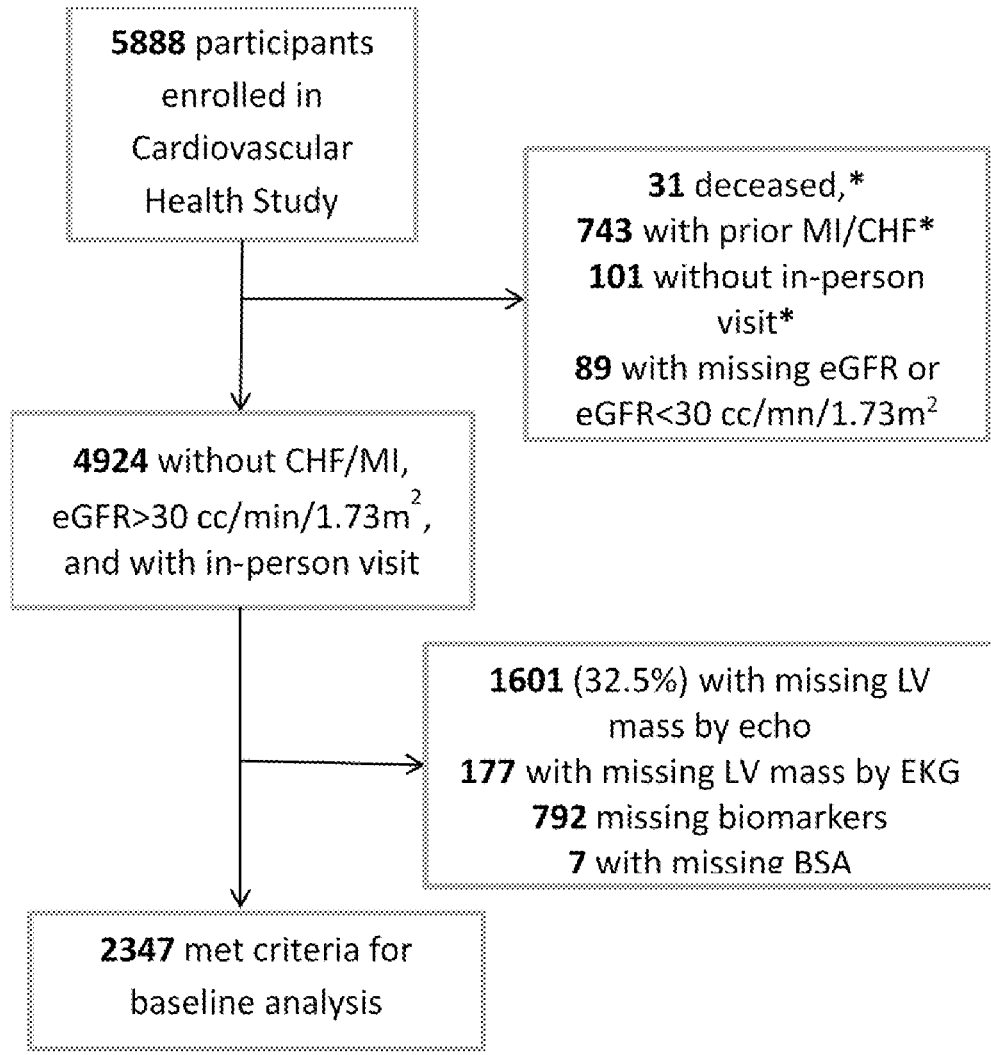
FIG. 4. Flow Diagram: study participants included in analysis of baseline biomarker levels.

Study Participants:

Among 2347 participants included in the baseline biomarker analyses (FIG. 4), 294 (12.5%) had LVH, among whom 210 had eccentric and 84 concentric LVH. Prevalence of LVH across progressive NT-proBNP tertiles was 8.6%, 10.9%, and 18.1% (p<0.001); and across hs cTnT tertiles was 8.5%, 11.9%, and 19.3%, (p<0.001). Hypertension was present in 74% of those with LVH and 55% without.

Table 1 shows baseline clinical and echocardiographic characteristics, stratified by hs cTnT and presence of LVH. Those with greater hs cTnT were older, more likely to be male, have diabetes, abnormal LVEF, an eGFR<60 cc/min/1.73 m$^2$, and higher blood pressure and body mass index. Similar trends across hs cTnT were noted for those with and without LVH. Among subjects without LVH, those with higher NT-proBNP were less likely to be African-American and more likely to have coronary heart disease, an eGFR<60 cc/min/1.73 m$^2$, an abnormal LVEF, higher blood pressure and body mass index (table 6). Similar trends, though typically not significant, were observed among those with LVH. Correlations of NT-proBNP (and hs-cTnT with LVMI at baseline were only modest (ρ=0.12 and ρ=0.21, respectively).

Association of LVH and Baseline Cardiac Biomarker Levels with Incident HF

Figure 1B:
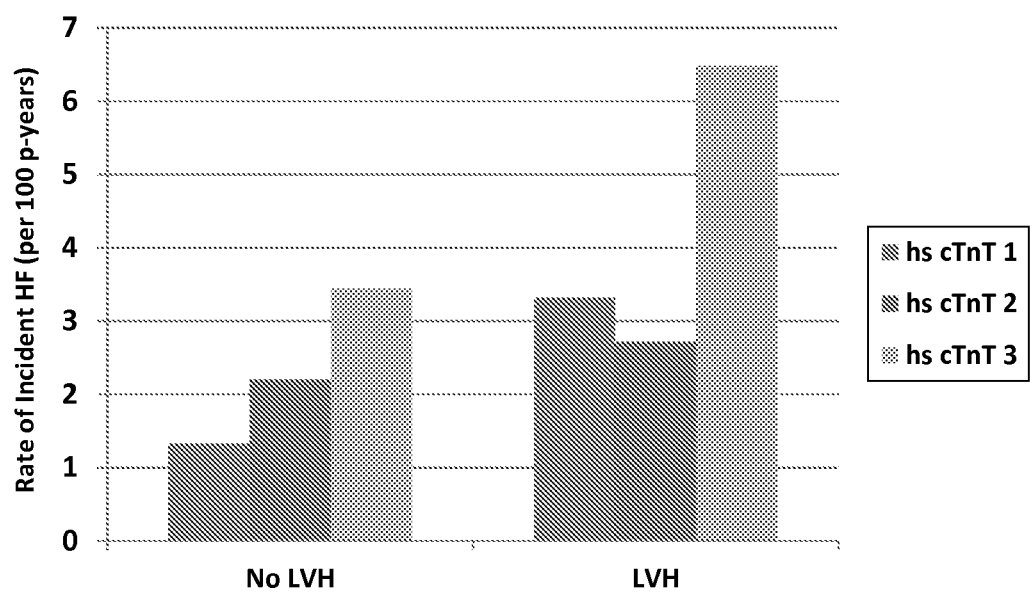

A total of 643 incident HF events occurred during a median 13.1 years (interquartile range; 7.1, 18.0) of follow-up. The rate of incident HF varied markedly between those with and without LVH (p<0.001) and by tertile of NT-proBNP and hs cTnT (p<0.001 for both; FIGS. 1a and 1b, respectively). Those participants with LVH and in the highest NT-proBNP tertile were more than four times as likely to have incident HF compared with those without LVH and in the lowest NT-proBNP tertile (Table 2: HR=4.42, 95% confidence intervals [CI]: 3.28, 5.94). Adjustment for demographic factors, co-morbidity, RWT and LVEF attenuated this association only modestly (HR=3.78, 95% CI: 2.78, 5.15). In contrast, those with LVH, but in the lowest NT-proBNP tertile were only at 1.71 (95% CI: 1.10, 2.67) times the risk of incident HF compared to those without LVH, after adjustment. Those participants with LVH and the highest tertile of hs cTnT were at nearly 6 times higher risk of HF compared to those without LVH and in the lowest hs-cTnT tertile (Table 2, 5.88, 95% CI: 4.37, 7.90). This association was attenuated only moderately after adjustment for potential confounders (adjusted HR=3.86, 95% CI: 2.84, 5.26).

Similar results were observed when LVMI was used in place of LVH (table 6). Compared to those in the lowest tertiles of LVMI and biomarker levels, those in the highest tertile of LVMI and biomarkers had 3.4 (NT-proBNP) and 3.3 times (hs cTnT) the risk of incident HF, after adjustment for potential confounders. In a competing risks model accounting for all-cause mortality the associations found in Table 2 were only slightly attenuated and all remained significant (Table 8). Among those with LVH, additional adjustment for residual differences in LVMI did not change the associations of either biomarker with incident HF (Δβ<5% for both markers). Among those with LVH, the addition of either hs cTnT or NT-proBNP (as continuous variables) significantly increased model discrimination, and the addition of hs cTnT significantly improved risk reclassification for incident HF at 10 years when added to traditional risk factors, LVEF, and RWT (table 9).

LVH, Cardiac Biomarkers, and Incidence of HFrEF Versus HFpEF

Figure 2A:
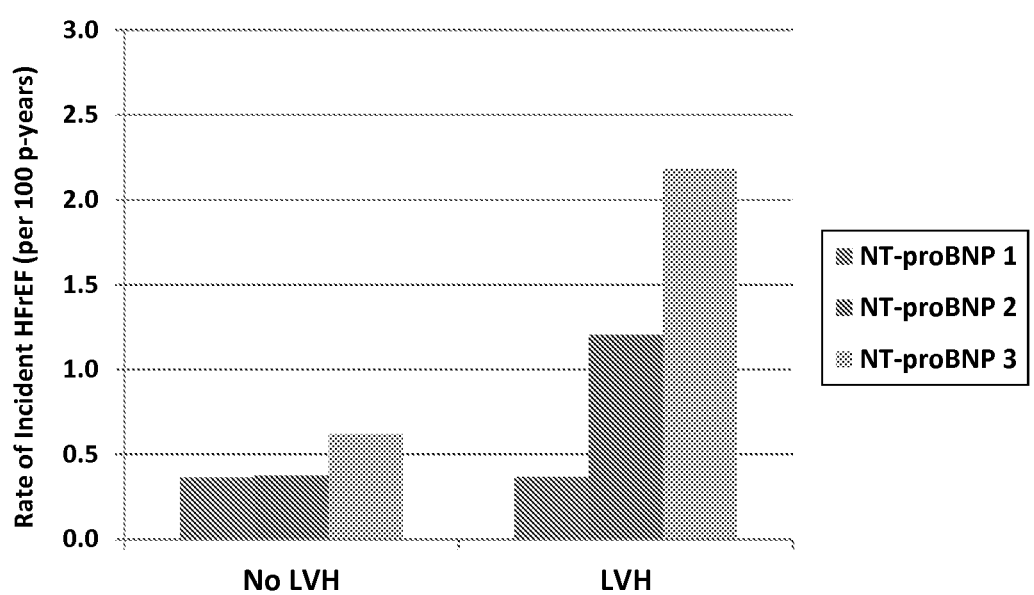
FIG. 2. Rate of incident HFrEF, by LVH and tertile of NT-proBNP (a) or hs cTnT (b).
Figure 2B:
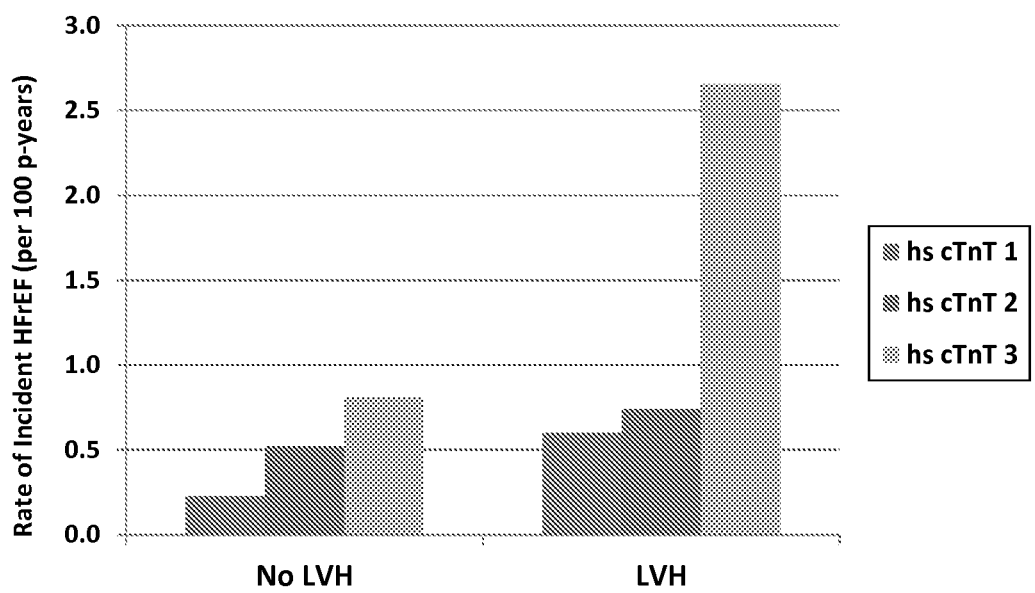

Among incident HF events, 215 (33.4%) had documented preserved EF, 150 (23.3%) had reduced EF, and 278 (43%)

had no documented EF at the time of incident HF diagnosis. Among those with incident HFrEF, 37 (24.7%) had LVH at baseline. The rate of incident HF with HFrEF differed significantly by tertile of NT-proBNP among those without (p=0.01) and with (p=0.001) LVH (FIG. 2a). The absolute difference in HFrEF rates by NT-proBNP tertile was greater among those with LVH. Similar results were noted for tertiles of hs cTnT, with a markedly greater risk of HFrEF among those with LVH and the highest tertile of hs cTnT (FIG. 2b). After adjustment for potential confounders, those participants with LVH in the highest tertile of NT-proBNP had a 5-fold greater risk of incident HFrEF (Table 3: HR=5.06, 95% CI: 2.89, 8.86), and those with LVH in the highest tertile of hs cTnT were at 7.8 times the risk of incident HFrEF versus those without LVH in the lowest hs cTnT level tertile (HR=7.83, 95%: 4.43, 13.83).

Figure 3A:
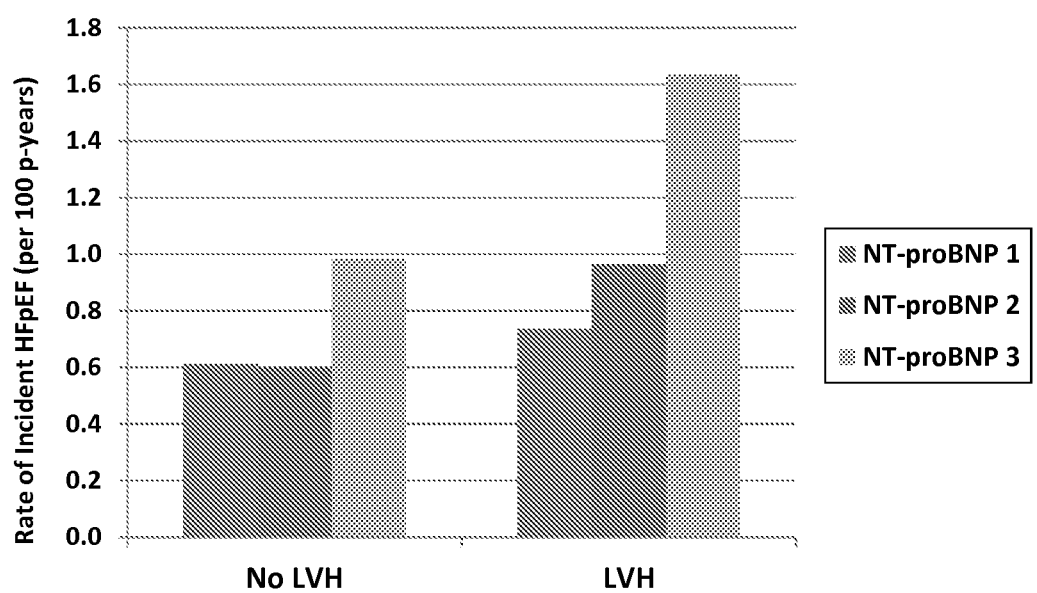
FIG. 3. Rate of incident HFpEF, by LVH and tertile of NT-proBNP (a) or hs cTnT (b).
Figure 3B:
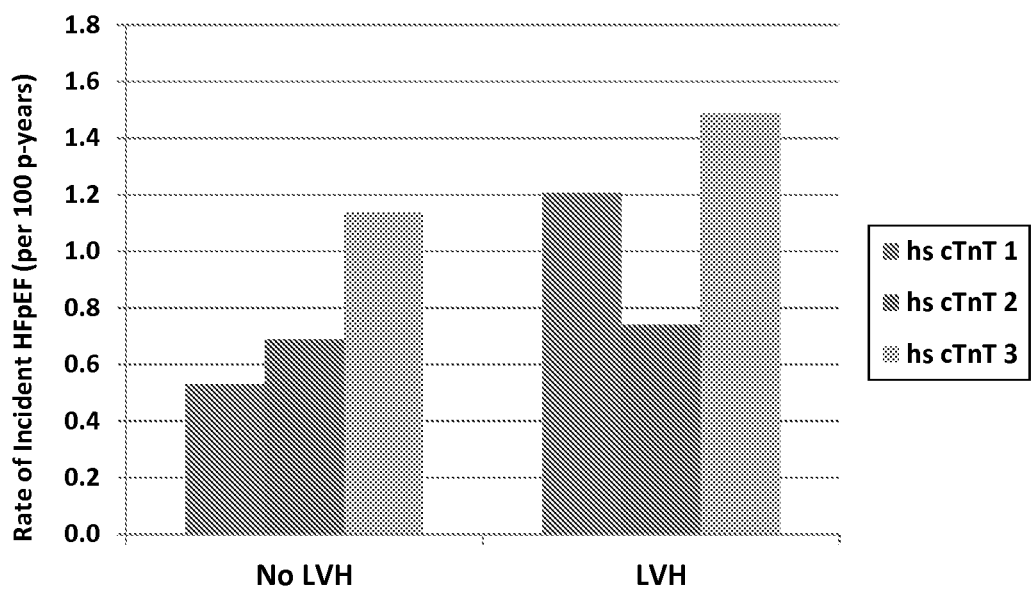
Figure 5A:
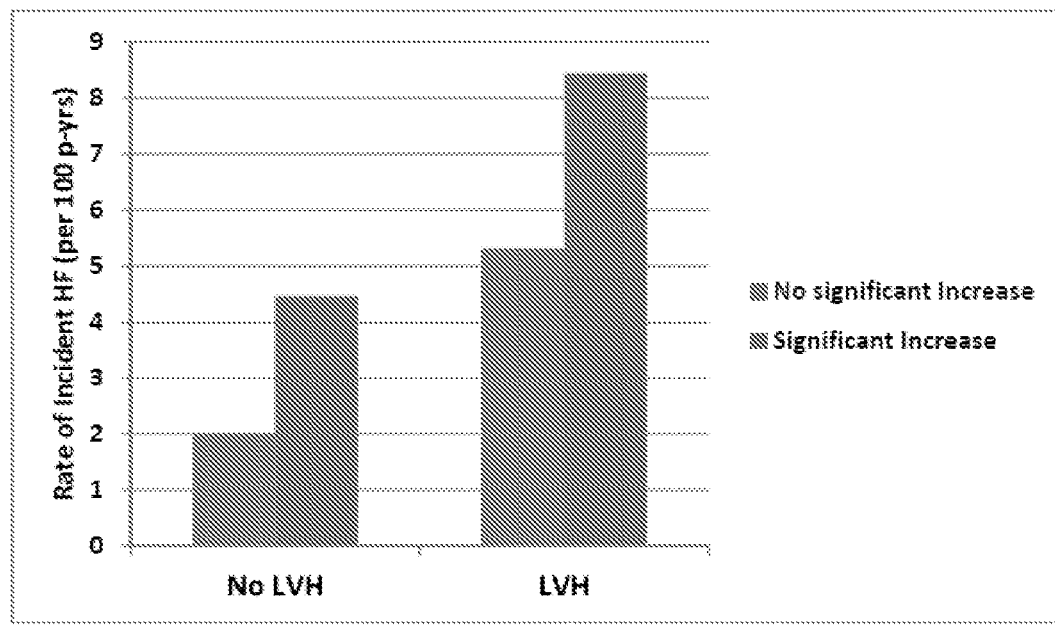
FIG. 5. Rate of incident heart failure, by left ventricular hypertrophy and significant increase in NT-proBNP (a) or hs-TnT (b). Definition of significant increase for each biomarker described in Examples.
Figure 5B:
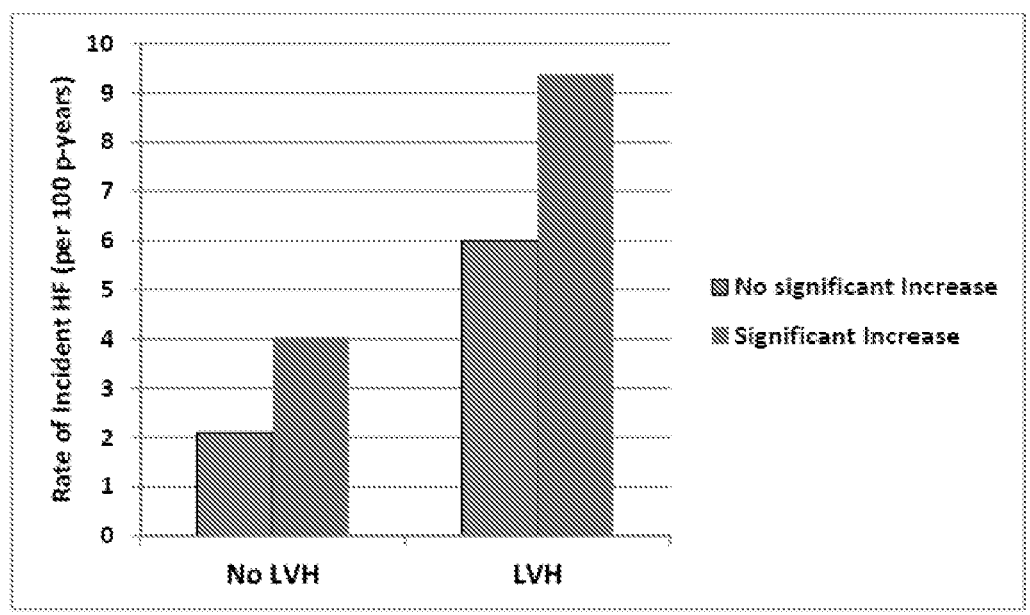
Figure 6:
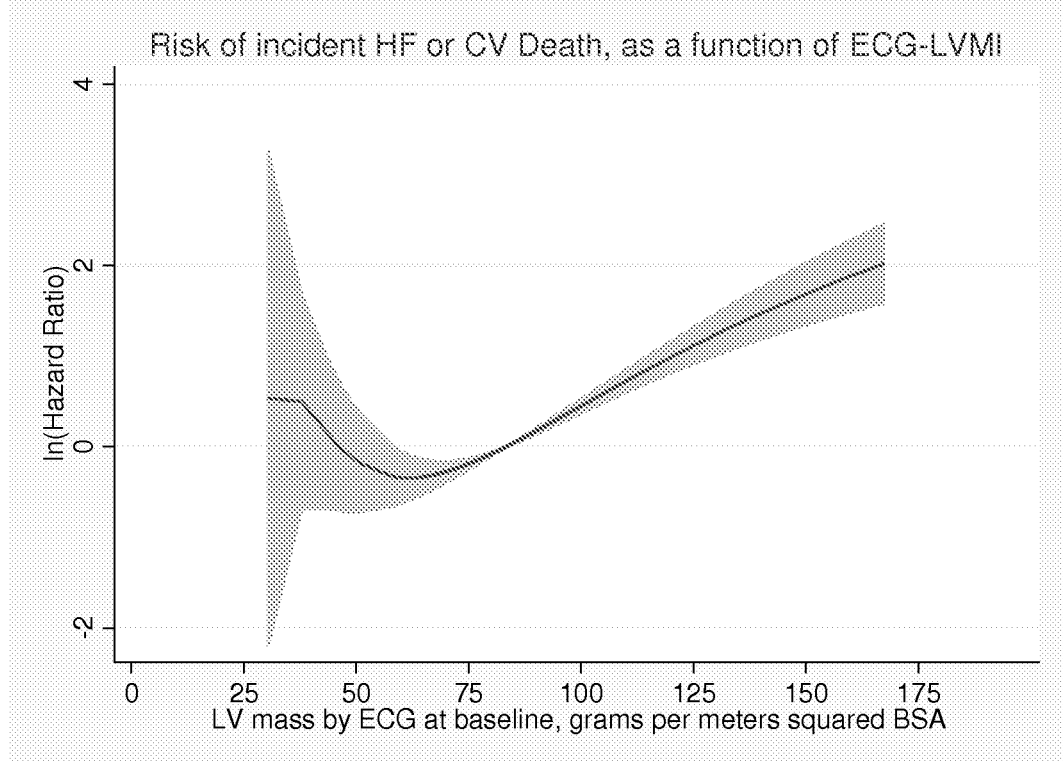
FIG. 6. Association of LV mass index by ECG with incident HF or CV death. The Y-axis represents the ln (Hazard ratio), adjusted for age, gender, and race. Zero on the Y-axis represents a Hazard ratio of 1.0.

Among those with incident HFpEF, 32 (15.0%) had LVH at baseline. Rate of incident HFpEF also differed significantly by tertile of NT-proBNP level among those without (p=0.003) and with (p=0.02) LVH (FIG. 3a). After adjustment for potential confounders, those with LVH and in the highest tertile of NT-proBNP were at approximately 3-fold greater risk of HFpEF compared to those without LVH and with the lowest NT-proBNP (HR=3.11, 95% CI: 1.80, 5.37; table 10). Similar results were observed for hs cTnT and LVH with regards to risk of HFpEF (FIG. 3b; table 10).
LVH, Change in Biomarker Levels and Incident HF A total of 1474 subjects had complete measures of change in biomarkers, complete LV mass measures on the 1994-95 echocardiogram and were without HF, MI, or eGFR<30 cc/min/1.73 m². Of these, 193 (13.1%) had LVH. Participants with LVH and a significant increase of either NT-proBNP or hs cTnT level had markedly higher rates of incident HF (FIGS. 5a and 5b; p<0.001 for both biomarkers) compared to those without LVH and with stable or declining biomarker levels. After adjustment for baseline NT-proBNP and risk factors, there remained a nearly 3-fold increased risk for incident HF when NT-proBNP level increased in those with LVH (Table 4). In contrast, those with LVH, but without an increasing NT-proBNP level were not at significantly greater risk of incident HF. Compared to those with stable or declining hs cTnT without LVH, those with LVH and an increase in hs cTnT level were at a 3.1-fold greater risk of incident HF, after adjustment for baseline hs cTnT and risk factors. Similar results were observed using LVMI in place of LVH (Supplemental table 6). In sensitivity analyses, we examined whether the relationship between change in biomarkers and incident HF among those with LVH was explained by residual differences in left ventricular mass between those with and without biomarker increases. Among those with LVH, significant increases of NT-proBNP or hs cTnT were associated with markedly greater HF risk even after additional adjustment for LVMI (as a continuous variable).

An additional analysis was done to determine the risk of HFrEF and HFpEF based on a rise in biomarker level and the presence or absence of LVH. Compared with individuals without LVH and with no increase in NT-proBNP levels, a rise in NT-proBNP among those with LVH was associated an adjusted HR of 3.46 (95% CI: 1.56, 7.65) for HFrEF but no significant increase in the risk for HFpEF (table 5 and supplemental table 7, respectively). Similarly, compared with individuals without LVH and with no increase in hs cTnT, a rise in hs cTnT in the subgroup with LVH was associated with an adjusted HR of 6.95 (95% CI: 3.07, 15.72) for HFrEF but no increase in the risk for HFpEF (table 5 and supplemental table 7, respectively).

Discussion

Among community-dwelling older adults without prior HF or MI, the HF risk associated with LVH was heterogeneous and strongly influenced by baseline levels and changes in NT-proBNP and hs cTnT, biomarkers of subclinical hemodynamic stress and myocardial injury, respectively. Unique to this study was our finding that baseline biomarker elevation appeared to associate with increased risk for progression to HFrEF to a greater extent than HFpEF among those with LVH. The stratification of risk for progression to HFrEF was even more powerful when evaluating longitudinal change in cardiac specific biomarker levels. For example, a rise of >50% in hs cTnT level in combination with LVH was associated with a nearly seven-fold adjusted greater risk of HFrEF, while the same combination of both LVH and an increasing hs cTnT conferred no increased risk for HFpEF. By following longitudinal change, each subject can in effect act as their own control, allowing characterization of the dynamic processes that result in progression from asymptomatic structural heart disease to symptomatic HF.

The implications of our findings are potentially two-fold. First, this study provides clinical data to support a recently proposed paradigm that identifies distinct pathophysiologies for HFrEF and HFpEF. Paulus et al. J Am Coll Cardiol. 2013; 62:263-271. Second, the results of this study may provide a rationale to develop and test a preventive strategy utilizing cardiac specific biomarkers and cardiac imaging to identify asymptomatic older adults at highest risk for progression to HFrEF. Though often presenting with similar signs and symptoms, there has been debate as to the degree of commonality of pathophysiology between HFrEF and HFpEF. Borlaug et al. Circulation. 2011; 123:2006-2013; discussion 2014. Our findings provide support to the contention that if HFpEF is preceded by myocyte cell hypertrophy, it is without cell death, whereas HFrEF, though potentially preceded by hypertrophy, is also associated with progressive myocyte death and increased wall stress. Paulus et al. J Am Coll Cardiol. 2013; 62:263-271; Gonzalez et al. J Am Coll Cardiol. 2011; 58:1833-1843. This hypothesis is supported by the differences in HF prediction associated with longitudinal change in biomarker levels, which may reflect not only the background milieu of cardiovascular risk factors, but also the pace of asymptomatic myocyte loss and increasing wall stress.

We have previously shown that changes in NT-proBNP and hs cTnT were associated with incident HF and cardiovascular death. deFilippi et al. J Am Coll Cardiol. 2010; 55:441-450; deFilippi et al. Jama. 2010; 304:2494-2502. Supporting the concept that myocyte loss—reflected in increases of these biomarkers—is critical to the progression of symptomatic HF, we also demonstrated in older adults with initial low levels of hs cTnT and NT-proBNP and a normal LVEF, that a rise in one or both biomarkers was associated with an increased incidence of progression to asymptomatic reduced LVEF. Glick et al. JACC: Heart Failure. 2013; 1:353-360. Histologic findings from myocardial biopsies also support evidence of greater myocyte cell loss in those with HFrEF compared to HFpEF. van Heerebeek et al. Circulation. 2006; 113:1966-1973. In contrast, HFpEF was associated with greater myocyte hypertrophy versus HFrEF irrespective of the extent of collagen deposition. van Heerebeek et al. Circulation. 2006; 113:1966-1973.

LVH Subtype and HF Risk

LVH is a well-known structural intermediary in the progression of hypertension to HF. Drazner M H. Circulation. 2011; 123:327-334; Aurigemma et al. *J Am Coll Cardiol.* 2001; 37:1042-1048. However, the progression of LVH to either an abnormal LVEF or symptomatic HF is heterogeneous and cannot be explained on the basis of hypertension alone. Drazner M H. Circulation. 2011; 123:327-334. In other cohorts, dividing LVH into concentric versus eccentric subtypes only moderately differentiated participants at increased risk of HFpEF versus HFrEF. Ho et al. Circ Heart Fail. 2013; 6:279-286. This lack of prognostic utility may be secondary to the current two-tiered classification of LVH, which does not account for the presence or absence of LV dilation. Khouri et al. Circ Cardiovasc Imaging 2010; 3:164-171. In the current study, we did not find that NT-proBNP nor hs cTnT were associated with RWT or greater LV mass in those with LVH, nor was there a difference in HFrEF or HFpEF risk by LVH subtype. Overall, our findings suggest that risk stratification among those with LVH may be better achieved by biochemical phenotyping as compared to stratification by relative wall thickness.

Clinical Implications

Current guidelines for hypertension and appropriateness criteria for cardiac imaging do not recommend screening for LVH in hypertensive patients or differentiating treatment based on its presence. Douglas et al. J Am Soc Echocardiogr. 2011; 24:229-267; James et al. 2014 evidence-based guideline for the management of high blood pressure in adults: Report from the panel members appointed to the eighth joint national committee (jnc 8). Jama. 2013. This is in large part based on the low positive predictive value of LVH for HF and no obvious change in treatment strategy based on its identification. However, we and others have previously identified that elevated levels of cardiac specific biomarkers in the presence of LVH stratifies these subjects as particularly high-risk HF. Neeland et al. J Am Coll Cardiol. 2013; 61:187-195; Olsen et al. Journal of hypertension. 2006; 24:1531-1539. With extension of this finding in the present study that now identifies HFrEF as a primary sequela of elevated or rising cardiac specific biomarker levels in the presence of LVH in older adults, specific therapies could be considered. In asymptomatic patients with reduced LVEF, ACE inhibitors reduce the progression to symptomatic HF and along with beta blockers remain a class I indication for treatment. Yancy et al. Circulation. 2013; 128:e240-319. In patients with LVH and systolic hypertension, an angiotension receptor blockade (ARB) was superior to beta-blockers to prevent a variety of cardiovascular outcomes including HF. Kjeldsen et al. Jama. 2002; 288:1491-1498. Further implicating the activation of the renal angiotensin aldosterone system as an upstream mechanism resulting in biochemical measures of myocyte loss and progression to HFrEF are findings from the HOPE study in normotensive vascular risk patients, where a higher dose of ramipril prevented a decrease in LVEF and increase in LV dimensions compared to either a low-dose or placebo. Lonn et al. J Am Coll Cardiol 2004; 43:2200-6. We suggest that our findings provide a basis for identifying older adults who could be targeted for HF prevention with renin-angiotensin-aldosterone system (RAAS) antagonism irrespective of whether they have hypertension. Furthermore, even many patients with hypertension may not be treated with an ACE inhibitor or angiotensin receptor blocker (ARB), and if they are treated, the doses can be low and there may be benefit to upward titration. For example, testing a biomarker strategy to modify care, the STOP-HF trial found intensifying management in primary care patients with at least one cardiovascular risk factor based on mild elevations in BNP resulted in a trend towards reduced new-onset HF. Ledwidge et al. Jama. 2013; 310:66-74. These results were in large part driven by differences in the utilization of ACE inhibitors and ARBs in patients with a known BNP>50 pg/mL, compared to the control group with a BNP value >50 pg/mL where the values were unknown to the clinician or patient. Further refining this strategy by evaluating for LVH and measuring NT-proBNP or hs cTnT could identify a high-risk cohort for progression to HFrEF in which specific therapies may be beneficial. A pilot and feasibility study of this approach for primary HF prevention is currently being developed. Lifestyle interventions may also be efficacious, as we have shown in a randomized pilot study that a year of physical activity in previously sedentary older adults significantly blunts a rise in hs cTnT level. deFilippi et al. Circulation. 2013; 128:A16937. Greater attention to medical and lifestyle interventions could reduce progression to symptomatic HF in this high-risk cohort with LVH and elevated or rising cardiac specific biomarker levels.

Limitations

LV mass measures were missing in approximately $1/3^{rd}$ of participants, with missing measures more likely among older male subjects and those with CV risk factors. Gardin et al. Circulation. 1995; 91:1739-1748. This differential lack of LV mass data may have led to biased estimates of the association with incident HF. However, the fact that these associations persisted after adjustment for demographics and risk factors, and are consistent with our prior findings in younger adults with LVH, suggests these associations are robust. Biomarkers were missing in an additional 25% of participants; as previously reported; those with complete biomarker measurements differed modestly from those with missing measurements, which could have also introduced bias. deFilippi et al. J Am Coll Cardiol. 2010; 55:441-450; deFilippi et al. Jama. 2010; 304:2494-2502. We only measured 2 biomarkers, and other biomarkers may have better prognostic utility for HFpEF. Lastly, measures of LVEF at incident HF were incomplete and were not adjudicated by a core echocardiography laboratory, which may have biased the results of associations with HF subtype. However, based on the large number of events with point-of-care echocardiograms, it is unlikely that the robust differences in the prediction of HFrEF versus HFpEF based on biomarkers and LVH would be nullified. Finally, no statistical adjustments to the type I error rate were made for multiple testing, and we cannot exclude a false positive finding.

Conclusion

LVH, as measured by echocardiography, was present in a substantial minority of older adults, particularly in those with elevated levels of NT-proBNP and hs cTnT. The presence of LVH and elevated or rising biomarker levels, independent of risk factors and subclassification of LVH, identified participants at high-risk for new-onset HF, particularly HFrEF. These findings identify a cohort of community dwelling individuals who may ultimately benefit from careful follow-up and consideration of specific medical and lifestyle interventions to prevent progression to symptomatic HF.

TABLE 1

Characteristics of study participants at baseline, by LVH and initial hs cTnT (N = 2347)

| | No LVH | | | | LVH | | | |
|---|---|---|---|---|---|---|---|---|
| | Tertile 1 | Tertile 2 | Tertile 3 | Test for trend | Tertile 1 | Tertile 2 | Tertile 3 | Test for trend |
| N | 932 | 584 | 535 | | 87 | 79 | 128 | |
| Range (pg/mL)* | | | | | | | | |
| Men | <3.00-4.82 | 4.84-9.23 | 9.32-43.89 | | <3.00-4.73 | 5.29-7.78 | 9.80-49.60 | |
| Women | <3.00 | 3.00-6.00 | 6.02-36.12 | | <3.00 | 3.12-5.98 | 6.55-71.82 | |
| Age (years) | 71.2 (4.6) | 72.7 (5.1) | 73.1 (5.6) | <.001 | 71.5 (4.4) | 73.7 (5.8) | 73.8 (5.9) | .006 |

TABLE 1-continued

Characteristics of study participants at baseline, by LVH and initial hs cTnT (N = 2347)

|  | No LVH | | | | LVH | | | |
| --- | --- | --- | --- | --- | --- | --- | --- | --- |
|  | Tertile 1 | Tertile 2 | Tertile 3 | Test for trend | Tertile 1 | Tertile 2 | Tertile 3 | Test for trend |
| Male | 247 (26.5%) | 250 (42.8%) | 216 (40.4%) |  | 24 (27.6%) | 29 (36.7%) | 61 (47.7%) |  |
| African-American | 143 (15.4%) | 74 (12.7%) | 88 (16.5%) | 0.8 | 12 (13.8%) | 8 (10.1%) | 16 (12.5%) | 0.8 |
| Diabetes | 92 (9.8%) | 90 (15.4%) | 119 (22.2%) | <.001 | 12 (13.8%) | 9 (11.4%) | 28 (21.9%) | .01 |
| Coronary Heart Disease | 78 (8.4%) | 65 (11.1%) | 58 (10.8%) | 0.09 | 7 (8.0%) | 15 (20.3%) | 21 (16.4%) | 0.13 |
| Body Mass Index | 26.1 (4.1) | 26.3 (4.4) | 27.0 (4.8) | <.001 | 26.4 (4.4) | 27.4 (4.7) | 27.1 (4.7) | 0.5 |
| SBP | 132.4 (19.8) | 133.6 (20.3) | 140.1 (22.5) | <.001 | 139.2 (22.8) | 143.8 (19.6) | 144.9 (24.0) | .07 |
| DBP | 70.2 (10.3) | 70.4 (10.8) | 71.4 (11.4) | 0.06 | 71.4 (11.6) | 72.2 (11.2) | 70.9 (13.2) | 0.7 |
| HTNive medications | 330 (35.4%) | 245 (42.0%) | 277 (52.0%) | <.001 | 39 (44.8%) | 46 (58.3%) | 76 (59.4%) | .04 |
| Smoking |  |  |  |  |  |  |  |  |
| Current | 112 (12.0%) | 51 (8.7%) | 51 (9.6%) | 0.9 | 13 (13.9%) | 6 (7.6%) | 16 (12.5%) | 0.12 |
| Former | 363 (39.0%) | 260 (44.6%) | 208 (39.0%) |  | 24 (27.6%) | 25 (31.7%) | 55 (43.0%) |  |
| Never | 455 (48.9%) | 272 (46.7%) | 275 (51.5%) |  | 50 (57.5%) | 48 (60.8%) | 57 (44.5%) |  |
| eGFR$_{MDRD}$ <60 | 132 (14.2%) | 100 (17.1%) | 148 (27.7%) | <001 | 8 (9.2%) | 17 (21.5%) | 41 (32.0%) | <.001 |
| Abnormal LVEF† | 4 (0.4%) | 5 (0.9%) | 7 (1.3%) | .06 | 1 (1.2%) | 2 (2.5%) | 14 (10.9%) | .002 |
| Relative Wall Thickness | 0.34 [0.30, 0.39] | 0.35 [0.30, 0.40] | 0.35 [0.30, 0.40] | 0.003 | 0.35 [0.28, 0.43] | 0.38 [0.31, 0.42] | 0.37 [0.30, 0.43] | 0.06 |
| LVMI (g/m²) |  |  |  |  |  |  |  |  |
| Male | 82.6 [71.5, 92.9] | 82.7 [68.5, 96.2] | 81.6 [69.8, 95.3] | 0.9 | 129.2 [119.8, 147.5] | 131.7 [126.2, 138.8] | 128.5 [121.4, 152.4] | 0.9 |
| Female | 71.3 [62.4, 80.5] | 72.4 [61.7, 81.7] | 73.8 [64.2, 85.1] | .04 | 106.4 [103.0, 122.4] | 112.8 [103.4, 121.0] | 113.1 [104.7, 123.1] | 0.1 |

Cell values represent mean (SD), N(%), or median[interquartile range].
*Biomarker categories are stratified by age and gender; range for age 70-75 years shown.
†LVEF <45% on initial echocardiogram.

TABLE 2

Risk of Incident HF, by LVH and initial biomarker level

| LVH by echo | Tertile of NT-proBNP | Hazard Ratios (95% CI) | |
| --- | --- | --- | --- |
|  |  | Unadjusted | Risk-factor adjusted* |
| None | 1 | 1.0 | 1.0 |
|  | 2 | 1.22 (0.96, 1.50) | 1.22 (0.97, 1.52) |
|  | 3 | 2.03 (1.64, 2.50) | 1.94 (1.56, 2.41) |
| Yes | 1 | 1.87 (1.20, 2.91) | 1.71 (1.10, 2.67) |
|  | 2 | 2.52 (1.69, 3.76) | 2.07 (1.38, 3.10) |
|  | 3 | 4.42 (3.28, 5.94) | 3.78 (2.78, 5.15) |

| LVH by echo | Tertile of hs cTnT | Unadjusted | Risk-factor adjusted* |
| --- | --- | --- | --- |
| None | 1 | 1.0 | 1.0 |
|  | 2 | 1.69 (1.36, 210) | 1.36 (1.09, 1.69) |
|  | 3 | 2.75 (2.23, 3.38) | 2.07 (1.67, 2.56) |
| Yes | 1 | 2.62 (1.80, 3.81) | 2.31 (1.58, 3.36) |
|  | 2 | 2.20 (1.41, 3.44) | 1.70 (1.08, 2.66) |
|  | 3 | 5.88 (4.37, 7.90) | 3.86 (2.84, 5.26) |

*Risk-Factor Adjusted: Age, race, gender, smoking, hypertension, diabetes, coronary heart disease, body mass index, eGFR <60 cc/min/1.73 m², LVEF <45%, and relative wall thickness (RWT).
Interaction of LVH with: NTproBNP: p = 0.5; hs cTnT: p = 0.6

TABLE 3

Risk of Heart failure with reduced EF, by LVH and initial biomarker level

| LVH by echo | Tertile of NT-proBNP | Hazard Ratios (95% CI) | |
| --- | --- | --- | --- |
|  |  | Unadjusted | Risk-factor adjusted* |
| None | 1 | 1.0 | 1.0 |
|  | 2 | 1.03 (0.64, 1.65) | 1.00 (0.62, 1.62) |
|  | 3 | 1.74 (1.11, 2.21) | 1.66 (1.05, 2.62) |
| Yes | 1 | 1.03 (0.64, 1.65) | 0.93 (0.28, 3.04) |
|  | 2 | 3.49 (1.72, 70.6) | 2.92 (1.42, 5.99) |
|  | 3 | 6.48 (3.82, 10.97) | 5.06 (2.89, 8.86) |

| LVH by echo | Tertile of hs cTnT | Unadjusted | Risk-factor adjusted* |
| --- | --- | --- | --- |
| None | 1 | 1.0 | 1.0 |
|  | 2 | 2.30 (1.42, 3.73) | 1.77 (1.08, 2.89) |
|  | 3 | 3.64 (2.29, 5.80) | 2.62 (1.62, 4.21) |
| Yes | 1 | 2.70 (1.12, 6.51) | 2.19 (0.90, 5.32) |
|  | 2 | 3.38 (1.40, 8.14) | 2.65 (1.10, 6.46) |
|  | 3 | 12.94 (7.5, 22.23) | 7.83 (4.43, 13.83) |

*Risk-Factor Adjusted: Adjustment covariates same as for Table 2. Interaction of LVH with: NT-proBNP tertiles: p = 0.07; hs-cTnT tertiles: p = 0.4

TABLE 4

Risk of Incident HF, by LVH and change in biomarkers (N = 1474)

| LVH by Echo | Increase in NT-proBNP | % of LVH subgroup | Hazard Ratios (95% CI) Baseline-adjusted | Hazard Ratios (95% CI) Risk-factor adjusted* |
|---|---|---|---|---|
| None | No | 1046 (81.7%) | 1.0 | 1.0 |
|  | Yes | 235 (18.3%) | 1.51 (1.14, 2.00) | 1.33 (0.99, 1.80) |
| Yes | No | 129 (66.8%) | 1.39 (0.97, 1.99) | 1.22 (0.83, 1.78) |
|  | Yes | 64 (33.2%) | 3.56 (2.46, 5.15) | 2.90 (1.98, 4.27) |

| LVH by Echo | Increase in hs cTnT | % of LVH subgroup | Baseline-adjusted | Risk-factor adjusted* |
|---|---|---|---|---|
| None | No | 1062 (82.9%) | 1.0 | 1.0 |
|  | Yes | 219 (17.1%) | 2.15 (1.63, 2.84) | 1.88 (1.40, 2.50) |
| Yes | No | 144 (74.6%) | 1.71 (1.23, 2.39) | 1.51 (1.06, 2.16) |
|  | Yes | 49 (25.4%) | 4.27 (2.85, 6.38) | 3.08 (2.03, 4.67) |

Baseline-adjusted: Adjusted for baseline biomarker concentration.
*Risk-Factor Adjusted: Adjusted for baseline biomarker level, age, race, gender, smoking, hypertension, diabetes, coronary heart disease, body mass index, LVEF <45%, eGFR <60 cc/min/1.73 m$^2$, and RWT.
Interaction of LVH with: Increase in NT-proBNP: p = .04; Increase in hs-cTnT: p = 0.8

TABLE 5

Risk of Incident HF with reduced EF, by LVH and change in biomarker levels (N = 1474)

| LVH by Echo | Increase in NT-proBNP | % of LVH subgroup | Hazard Ratios (95% CI) Baseline-adjusted | Hazard Ratios (95% CI) Risk-factor adjusted |
|---|---|---|---|---|
| None | No | 1046 (81.7%) | 1.0 | 1.0 |
|  | Yes | 235 (18.3%) | 1.17 (0.60, 2.29) | 1.14 (0.55, 2.35) |
| Yes | No | 129 (66.8%) | 2.08 (1.07, 4.06) | 1.99 (0.97, 4.08) |
|  | Yes | 64 (33.2%) | 4.77 (2.36, 9.77) | 3.46 (1.56, 7.65) |

| LVH by Echo | Increase in hs cTnT | % of LVH subgroup | Baseline-adjusted | Risk-factor adjusted |
|---|---|---|---|---|
| None | No | 1062 (82.9%) | 1.0 | 1.0 |
|  | Yes | 219 (17.1%) | 2.65 (1.45, 4.86) | 2.48 (1.29, 4.77) |
| Yes | No | 144 (74.6%) | 2.87 (1.53, 5.39) | 2.21 (1.08, 4.54) |
|  | Yes | 49 (25.4%) | 6.94 (3.22, 14.96) | 6.95 (3.07, 15.72) |

Cell values are hazard ratios (95% CI) from Cox proportional hazards models.
Hazard ratios adjusted for: baseline biomarker level, age, race, gender, smoking, hypertension, diabetes, coronary heart disease, body mass index, eGFR <60 cc/min/1.73 m$^2$, relative wall thickness and LVEF <45%.
Interaction between LVH and Change in NT-proBNP: p = 0.5
Interaction between LVH and Change in hs-cTnT: p = 0.7

TABLE 6

Characteristics of study participants at baseline, by LVH and initial NT-proBNP (tertiles) (N = 2347)

| | No LVH | | | | LVH | | | |
|---|---|---|---|---|---|---|---|---|
| | Tertile 1 | Tertile 2 | Tertile 3 | Test for trend | Tertile 1 | Tertile 2 | Tertile 3 | Test for Trend |
| N | 712 | 698 | 643 | | 67 | 85 | 142 | |
| Range (pg/mL)* | | | | | | | | |
| Men | <5.0-58.6 | 58.7-130.5 | 131.3-1882 | | 21.0-56.9 | 60.4-124.7 | 136.5-3178 | |
| Women | <5.0-71.7 | 72.9-147.7 | 149.5-3248 | | <5.0-69.8 | 73.4-147 | 168.7-2570 | |
| Age (years) | 72.0 (4.9) | 72.0 (5.4) | 72.4 (5.4) | 0.13 | 71.7 (5.1) | 74.0 (4.7) | 73.2 (5.9) | 0.16 |
| Male | 253 (35.5%) | 247 (35.4%) | 215 (33.4%) | 0.5 | 21 (31.3%) | 30 (35.3%) | 63 (44.4%) | 0.06 |
| African-American | 142 (19.9%) | 95 (13.6%) | 69 (10.7%) | <.001 | 8 (11.9%) | 8 (9.4%) | 20 (14.1%) | 0.5 |
| Diabetes | 99 (15.7%) | 85 (14.0%) | 68 (12.9%) | 0.11 | 10 (17.2%) | 11 (16.9%) | 20 (18.7%) | 0.3 |

TABLE 6-continued

Characteristics of study participants at baseline, by LVH and initial NT-proBNP (tertiles) (N = 2347)

|  | No LVH | | | | LVH | | | |
|---|---|---|---|---|---|---|---|---|
|  | Tertile 1 | Tertile 2 | Tertile 3 | Test for trend | Tertile 1 | Tertile 2 | Tertile 3 | Test for Trend |
| Coronary Heart Disease[†] | 56 (7.9%) | 64 (9.2%) | 81 (12.6%) | 0.004 | 6 (9.0%) | 15 (17.%) | 23 (16.2%) | 0.25 |
| Body Mass Index | 26.8 (4.1) | 26.4 (4.4) | 26.0 (4.6) | .001 | 28.4 (4.9) | 26.5 (4.2) | 26.6 (4.6) | .02 |
| SBP | 131.0 (18.8) | 134.3 (20.2) | 139.6 (23.0) | <.001 | 140.3 (20.8) | 140.5 (18.2) | 145.6 (25.4) | .07 |
| DBP | 70.2 (10.5) | 70.2 (10.3) | 71.4 (11.4) | .03 | 71.8 (10.2) | 70.4 (10.7) | 71.9 (13.9) | 0.8 |
| HTN medications | 266 (37.4%) | 272 (39.1%) | 316 (49.2%) | <.001 | 36 (53.7%) | 42 (49.4%) | 83 (58.5%) | 0.4 |
| Smoking | | | | | | | | |
| Current | 112 (12.0%) | 51 (8.8%) | 51 (9.6%) | 0.2 | 6 (9.0%) | 7 (8.2%) | 22 (15.5%) | 0.06 |
| Former | 363 (39.0%) | 260 (44.6%) | 208 (39.0%) | | 19 (28.4%) | 34 (40.0%) | 51 (35.9%) | |
| Never | 455 (48.9%) | 272 (46.7%) | 275 (51.5%) | | 42 (62.3%) | 44 (51.8%) | 69 (48.6%) | |
| LDL cholesterol | 135.9 (35.7) | 129.9 (33.0) | 127.2 (36.1) | <.001 | 138.1 (32.8) | 131.2 (35.9) | 120.5 (28.6) | <.001 |
| HDL cholesterol | 55.5 (15.0) | 56.4 (16.3) | 56.9 (16.3) | 0.3 | 50.7 (11.4) | 51.3 (13.2) | 52.8 (15.9) | 0.3 |
| eGFR$_{MDRD}$ <60 cc/min/1.73 m$^2$ | 94 (13.2%) | 134 (19.2%) | 153 (23.8%) | <.001 | 6 (9.0%) | 19 (22.4%) | 41 (28.9%) | .001 |
| Abnormal LVEF[‡] | 2 (0.3) | 4 (0.4%) | 11 (1.7%) | .003 | 0 (0%) | 0 (0%) | 17 (12.0%) | <.001 |
| Relative Wall Thickness | 0.35 [0.30, 0.40] | 0.34 [0.30, 0.39] | 0.35 [0.30, 0.39 | 0.6 | 0.35 [0.28, 0.41] | 0.38 [0.32, 0.43] | 0.36 [0.30, 0.43] | 0.5 |
| LVMI (g/m$^2$) | | | | | | | | |
| Male | 79.4 [67.6, 91.1] | 83.5 [72.5, 95.0] | 84.0 [74.2, 99.2] | <.001 | 126.2 [121.6, 131.7] | 128.0 [121.3, 145.8] | 132.9 [124.0, 156.7] | .04 |
| Female | 71.1 [63.2, 80.7] | 73.2 [62.0, 8.23] | 73.2 [62.3, 82.7] | 0.2 | 111.0 [106.0, 122.4] | 108.6 [101.6, 118.9] | 111.9 [103.2, 123.0] | 0.9 |

Cell values represent mean (SD), N(%), or median[interquartile range].
*Biomarker categories are stratified by age and gender; range for age 70-75 years shown.
[†]Participants with prior myocardial infarction excluded
[‡]LVEF <45% on initial echocardiogram

TABLE 7

Risk of heart failure, by LVMI and initial biomarker levels

| LVMI tertile | 1 | 2 | 3 |
|---|---|---|---|
|  | NT-proBNP tertile | | |
| 1 | 1.0 (reference) | 1.14 (0.77, 1.67) | 1.84 (1.28, 2.65) |
| 2 | 0.99 (0.68, 1.45) | 1.34 (0.93, 1.94) | 1.64 (1.14, 2.37) |
| 3 | 1.49 (1.02, 2.17) | 1.62 (1.14, 2.31) | 3.39 (2.45, 4.69) |
|  | hs cTnT Tertile | | |
| 1 | 1.0 (reference) | 1.18 (0.82, 1.71) | 1.83 (1.27, 2.65) |
| 2 | 0.96 (0.68, 1.36) | 1.37 (0.94, 1.98) | 1.81 (1.26, 2.58) |
| 3 | 1.52 (1.07, 2.14) | 1.72 (1.21, 2.45) | 3.31 (2.41, 4.54) |

Cell values represent adjusted Hazard ratios (95% CI), adjusted for: Age, race, gender, smoking, hypertension, diabetes, coronary heart disease, body mass index, LVEF <45%, RWT, and eGFR <60 cc/min/1.73 m$^2$
Interaction between LVMI tertile and NT-proBNP tertile: p = 0.2
Interaction between LVMI tertile and hs-cTnT tertle: p = 0.6

TABLE 8

Risk of Incident HF, by LVH and initial biomarker level, accounting for competing risk of mortality

|  |  | Hazard Ratios (95% CI) | |
|---|---|---|---|
| LVH by echo | Tertile of NT-proBNP | Unadjusted | Risk-factor adjusted* |
| None | 1 | 1.0 | 1.0 |
|  | 2 | 1.20 (0.96, 1.49) | 1.20 (0.96, 1.51) |
|  | 3 | 1.86 (1.51, 2.30) | 1.75 (1.40, 2.18) |

TABLE 8-continued

Risk of Incident HF, by LVH and initial biomarker level, accounting for competing risk of mortality

| Yes | 1 | 1.88 (1.21, 2.92) | 1.70 (1.10, 2.64) |
|---|---|---|---|
|  | 2 | 1.97 (1.30, 2.97) | 1.62 (1.06, 2.49) |
|  | 3 | 2.99 (2.19, 4.09) | 2.43 (1.75, 3.38) |
| LVH by echo | Tertile of hs cTnT | Unadjusted | Risk-factor adjusted* |
| None | 1 | 1.0 | 1.0 |
|  | 2 | 1.60 (1.30, 1.98) | 1.40 (1.12, 1.74) |
|  | 3 | 2.40 (1.96, 2.95) | 1.94 (1.56, 2.40) |
| Yes | 1 | 2.43 (1.68, 3.51) | 2.25 (1.55, 3.27) |
|  | 2 | 1.72 (1.09, 2.72) | 1.29 (0.80, 2.07) |
|  | 3 | 3.75 (2.72, 5.14) | 2.67 (1.92, 3.71) |

*Risk-Factor Adjusted: Age, race, gender, smoking, hypertension, diabetes, coronary heart disease, body mass index, eGFR <60 cc/min/1.73 m$^2$, LVEF <45% and relative wall thickness.

TABLE 9

Reclassification and Discrimination for prediction of incident HF, among those with LVH (N = 293)

|  | NT-proBNP | hs-cTnT |
|---|---|---|
|  | IDI | |
|  | .0276 | .0273 |
| Continuous NRI | p = .02 | p = .01 |
| events | 0.143 | 0.152 |
|  | (−0.035, 0.333) | (−0.034, 0.333) |

TABLE 9-continued

Reclassification and Discrimination for prediction of incident HF, among those with LVH (N = 293)

|  | NT-proBNP | hs-cTnT |
|---|---|---|
|  | IDI | |
|  | .0276 | .0273 |
| Continuous NRI | p = .02 | p = .01 |
| non-event | 0.115 | 0.209 |
|  | (−0.056, 0.276) | (0.0412, 0.364) |
| Total | 0.257 | 0.380 |
|  | (−0.048, 0.536) | (0.058, 0.646) |

IDI: Integrated Discrimination Improvement; NRI: Net reclassification improvement for incident HF at 10 years (N = 95 events). Statistics compare biomarker + risk factors (defined in Table 2) to risk factors alone.

TABLE 10

Risk of Heart failure with preserved EF, by LVH and initial biomarker level

| | | Hazard Ratios (95% CI) | |
|---|---|---|---|
| LVH by echo | Tertile of NT-proBNP | Unadjusted | Risk-factor* adjusted |
| None | 1 | 1.0 | 1.0 |
|  | 2 | 0.97 (0.67, 1.41) | 0.99 (0.68, 1.44) |
|  | 3 | 1.68 (1.19, 2.39) | 1.63 (1.14, 2.33) |
| Yes | 1 | 1.22 (0.52, 2.83) | 1.10 (0.47, 2.57) |
|  | 2 | 1.82 (0.87, 3.81) | 1.52 (0.72, 3.21) |
|  | 3 | 3.34 (1.96, 5.70) | 3.11 (1.80, 5.37) |

TABLE 10-continued

Risk of Heart failure with preserved EF, by LVH and initial biomarker level

| LVH by echo | Tertile of hs cTnT | Unadjusted | Risk-factor* adjusted |
|---|---|---|---|
| None | 1 | 1.0 | 1.0 |
|  | 2 | 1.35 (0.93, 1.94) | 1.15 (0.79, 1.67) |
|  | 3 | 2.35 (1.67, 3.31) | 1.82 (1.29, 2.60) |
| Yes | 1 | 2.46 (1.33, 4.54) | 2.33 (1.25, 4.32) |
|  | 2 | 1.56 (0.68, 3.60) | 1.21 (0.52, 2.81) |
|  | 3 | 3.71 (2.07, 6.63) | 2.62 (1.44, 4.77) |

*Risk-Factor Adjusted: Baseline biomarker level, age, race, gender, smoking, hypertension, diabetes, coronary heart disease, body mass index, LVEF <45%, eGFR <60 cc/min/1.73 m$^2$, and RWT.
Interaction of LVH with: NT-proBNP tertiles: p = 0.3; hs cTnT tertiles: p = 0.3

TABLE 11

Risk of heart failure, by cross-classification of LVMI (sex-stratified tertile) and Increase in NT-proBNP or hs cTnT

| LVMI tertile | No | Yes |
|---|---|---|
| | Increase in NT-proBNP | |
| 1 | 1.0 (reference) | 1.32 (0.74, 2.38) |
| 2 | 1.58 (1.12, 2.22) | 1.26 (0.74, 2.15) |
| 3 | 1.52 (1.07, 2.16) | 3.35 (2.29, 4.90) |
| | Increase in hs cTnT | |
| 1 | 1.0 (reference) | 2.05 (1.19, 3.52) |
| 2 | 1.55 (1.10, 2.20) | 2.41 (1.45, 4.01) |
| 3 | 1.73 (1.22, 2.46) | 3.67 (2.46, 5.47) |

Cell values represent adjusted Hazard ratios (95% CI)
Associations adjusted for baseline biomarker level, age, race, gender, smoking, hypertension, diabetes, coronary heart disease, body mass index, LVEF <45%, and eGFR <60 cc/min/1.73 m$^2$, and relative wall thickness.
Interaction between LVMI tertile and Increase in NT-proBNP: p = 0.02
Interaction between LVMI tertile and Increase in hs cTnT: p = 0.7

TABLE 12

Risk of incident HF with preserved EF, by LVH and change in biomarker level (N = 1474)

| | | | Hazard Ratios (95% CI) | |
|---|---|---|---|---|
| LVH by Echo | Increase in NT-proBNP | % of LVH subgroup | Baseline- adjusted | Risk-factor adjusted |
| None | No | 1046 (81.7%) | 1.0 | 1.0 |
|  | Yes | 235 (18.3%) | 1.33 (0.82, 2.15) | 1.14 (0.69, 1.90) |
| Yes | No | 129 (66.8%) | 0.92 (0.46, 1.83) | 0.69 (0.33, 1.45) |
|  | Yes | 64 (33.2%) | 2.02 (0.93, 4.43) | 1.81 (0.82, 4.00) |
| LVH by Echo | Increase in hs cTnT | % of LVH subgroup | Baseline- adjusted | Risk-factor adjusted |
| None | No | 1062 (82.9%) | 1.0 | 1.0 |
|  | Yes | 219 (17.1%) | 1.76 (1.10, 2.83) | 1.38 (0.83, 2.28) |
| Yes | No | 144 (74.6%) | 1.13 (0.60, 2.12) | 0.98 (0.50, 1.91) |
|  | Yes | 49 (25.4%) | 2.05 (0.83, 5.07) | 1.21 (0.48, 3.04) |

Cell values are hazard ratios (95% CI) from Cox proportional hazards models.
Hazard ratios adjusted for baseline biomarker level, age, race, gender, smoking, hypertension, diabetes, coronary heart disease, body mass index, eGFR <60 cc/min/1.73 m$^2$, relative wall thickness and RWT.
Interaction between LVH and Change in NT-proBNP: p = .1
Interaction between LVH and Change in hs-cTnT: p = 0.9

Example 2

Combing ECG-defined LV Mass with Cardiac Biomarkers as a Prognostic Tool for Predicting Heart Failure and CV Death Measurement of Cardiac-Specific Biomarkers Measurement of high sensitivity troponin T (TnT) and N-terminal pro B-type Natriuretic Peptide (NT-proBNP) were performed on instrumentation manufactured by Roche Diagnostics Corporation, 9115 Hague Road, Indianapolis, Ind. 46250. Three instrumentation systems for these measurements are substantially equivalent for TnT and NT-proBNP quantification; these include the Cobas Elecsys 2010 (2010) analyzer, the Cobas e 411 (e 411) analyzer and the Cobas e 601 (e601) module. The 2010 and e411 systems consist of the analyzer section for sample processing and assay performance and a control unit which contains the software for the operation and control of the testing unit. Both the 2010 and e411 systems and are automated, random access benchtop analyzers for in vitro qualitative and quantitative in measurements. Assay reagent, calibrator and control information is entered into the systems by use of barcodes associated with specific reagents or downloaded through a link connection. The e 601 is the immunoassay module that is part the 6000 analyzer series from Roche Diagnostics. The analyzer portion of the e601 module contains components including a reagent area containing a reagent disk, a barcode reader, a capping/decapping mechanism, a microbead mixer, a reagent probe and rinse stations. The measuring area consists of an incubator, a sample probe, two sipper probes, two sipper rinse stations and two measuring cells. A pre-wash area serves to provide an area for preparing the samples for measurement by separating contents of the measurement solutions prior to washing. This analyzer area contains a tube gripper, a sipper, a dispenser, a rinse station, separation station and vortex mixing station. The instrument processes samples and then performs the immunoassay testing. The control unit of the 601 uses a graphic interface that operates all instrument functions. The system contains a PC that serves as a gateway link to retrieve and distribute data and information.

The 2010, e601 and e601 measure hs-TnT and NT-proBNP using the principle of sandwich immunoassay and ElectroChemiLuminescence (ECL) technology. The principle for these systems is formation of a 'sandwich' immunoassay complex in which antigen analyte (either TnT or NT-proBNP) is bound by two monoclonal antibodies, each targeting a different epitope location on the antigen analyte molecule. One of the monoclonal antibodies is bound to the substance biotin; the other analyte specific monoclonal antibody to a different epitope location is labeled with a Ruthenium complex for detection. During an initial incubation period, these two monoclonal antibodies are mixed with a sample containing the analyte (TnT or NT-proBNP), Because each antibodies has high affinity for a different epitope on the analyte molecule, a <biotinylated antibody-analyte-Ruthenium antibody> sandwich complex is formed during the initial incubation, in a second step, streptavidin coated paramagnetic beads are added to the same measurement cell and incubated, Because streptavidin and biotin form one of the strongest, most resilient non covalent bond in nature, the paramagnetic beads serve to capture the immune complex sandwich containing analyte (TnT or NT-proBNP). The reaction mixture is aspirated into a reaction cell where a magnetic field is applied, which causes the magnetic beads to bind to the surface of the measurement cell. Unbound substances are then removed by treatment with a solution (ProCell/ProCell M). This solution also provides tripropylamide, which is essential for the ECL reaction. Application of a voltage to the electrode induces chemiluminescent emission, which is measured by a photomultiplier tube. The concentration of each analyte (TnT or NT-proBNP) in samples is determined from a calibration curve which is instrument-specifically generated by a two point calibration a master curve provided by the reagent barcode.

TABLE 13

Rates (per 100 patient-years) and adjusted risk of HF or CV mortality among those with and without 2 of 3 elevated abnormal markers: ECG-LVH*, NT-proBNP, and/or hs cTnT, among all older adults (top rows) or older adults with hypertension (bottom rows).

| Eligibility | Subgroup | Percent of Study Sample | Rate of HF or CV mortality (per 100 patient-years) | Adjusted^ risk of HF or CV death |
|---|---|---|---|---|
| Older adults without prior HF | No LVH, Neither NT-proBNP nor hs cTnT elevated | 43.9% | 1.9 (1.6, 2.2) | 1.0 (reference) |
| | At least 2 of: High LVMI or high NT-proBNP or high cTnT | 20.0% | 6.7 (6.1, 7.4) | 2..81 (2.43, 3.24) |
| Older adults with Hypertension and without prior HF | No LVH, Neither NT-proBNP nor hs cTnT elevated | 36.6% | 2.9 (2.6. 3.4) | 1.0 (Reference) |
| | At least 2 of: High LVMI or high NT-proBNP or high cTnT | 33.1% | 6.7 (6.0, 7.4) | 3.00 (2.61, 3.46) |

*ECG LVH defined is based on the top 12.5% of ECG determined mass based on an echocardiography determined LVH prevalence of 12.5% in the same cohort.
^Adjusted for age, gender, race, diabetes, hypertension, coronary heart disease, body mass index, smoking, and estimated GFR <60 cc/min/1.73 m².

TABLE 14

Cut-points used to define "elevated" NT-proBNP and hs-cTnT (by age and gender) and ECG-LVH (by gender)

| Age (years) | NT-proBNP (pg/mL) | | hs-cTnT (pg/mL) | | ECG - Left Ventricular Mass Index (g/m²) | |
|---|---|---|---|---|---|---|
| | Men | Women | Men | Women | Men | Women |
| 65-69 | 93.2 | 122.4 | 7.54 | 6.06 | 102.7 | 88.7 |
| 70-74 | 130.5 | 147.7 | 9.23 | 6.00 | | |

TABLE 14-continued

Cut-points used to define "elevated" NT-proBNP and hs-cTnT
(by age and gender) and ECG-LVH (by gender)

| Age (years) | NT-proBNP (pg/mL) | | hs-cTnT (pg/mL) | | ECG - Left Ventricular Mass Index (g/m²) | |
|---|---|---|---|---|---|---|
| | Men | Women | Men | Women | Men | Women |
| 75-79 | 152.8 | 246.3 | 10.84 | 7.83 | | |
| 80+ | 304.9 | 341.2 | 16.61 | 11.07 | | |

Measurements above these cut-points are considered to define an "abnormal" level for the purposes of risk-stratification for incident Heart Failure and Cardiovascular Mortality
Methods and Cut-points for determining LVH by echocardiography. First, one estimates the expected LV mass based on previously published normative equations derived from the Cardiovascular Health Study (*Circulation* 1995; 91:1739-1748):
For women: Expected LV mass=$13.9*Weight^{0.51}$
For men: Expected LV mass=$16.6*Weight^{0.51}$
Where weight is in kilograms and LV mass is in grams.
Next, the measured LV mass is compared to expected LV Mass, if the ratio of measured>expected is >1.45, then the patient is considered to have left ventricular hypertrophy (LVH). That is, LVH is defined if the measured LV mass is more than 45% greater than what would be expected based on gender and body mass.
Methods for determining LV mass by electrocardiography: First, a 12-lead surface ECG is recorded according to standard methods for electrode placement. LV mass is estimated with gender- and race-specific equations from the Novacode program, widely used in epidemiologic studies and clinical trials (*J Electrocardiol.* 1991; 24:121-127)
White and black men: LVM=$-58.51+0.060*QS(III)+0.021*R(V_5)-0.033*QS(V_1)-0.296*Tp(aVR)+0.316*Tn(V_6)+1.821*QRS$.
White women: LVM=$134.77+0.023*R(V_5)-0.155*QS(I)+0.070*QS(V_5)+0.112*Tp(V_1)-0.123*Tp(V_6)+0.032*R(aVL)$.
Black women: LVM=$-90.71+0.050*R(I)-0.051*R(V_1)-0.098*QS(V_6)+0.522*Tn(I)+1.848*QRS+0.023*[R(V_6)+QS(V_2)]$.

All patents and publications mentioned and/or cited in this specification are indicative of the level of those skilled in the art to which the invention pertains. All patents and publications mentioned and/or cited herein are incorporated by reference to the same extent as if each individual publication was specifically and individually indicated as having been incorporated by reference in its entirety.

What is claimed is:

1. A method for predicting whether a human patient 65 years of age or older with left ventricular hypertrophy (LVH) is at increased risk for developing heart failure with reduced ejection fraction (HFrEF), comprising
   i) obtaining the results of an assay that measures levels of N-terminal pro B-type Natriuretic Peptide (NT-proBNP); and
   ii) obtaining the results of an assay that measures levels of cardiac troponin T;
   wherein the patient is at increased risk for heart failure with reduced ejection fraction (HFrEF) if
      a. the level of NT-proBNP is increased relative to a control, and the level of cardiac troponin T is increased relative to a control;
      b. the level of NT-proBNP is increased relative to a control; or
      c. the level of cardiac troponin T is increased relative to a control,
   wherein the method further comprises administering to the patient an effective amount of one or more ACE inhibitors, angiotensin receptor blockers, beta-blockers, and combinations thereof.

2. The method of claim 1, wherein the method comprises measuring an increase in NT-proBNP>25% from baseline to a final concentration of >190 pg/ml and/or an increase in cardiac troponin T>50% from baseline.

3. The method of claim 1, wherein if a patient has a cardiac troponin T value below 3 ng/L, a value of 2.99 ng/L is imputed as the baseline value.

4. The method of claim 1, wherein the LVH is determined by a method selected from the group consisting of echocardiography, magnetic resonance imaging and electrocardiography.

5. The method of claim 1, wherein the method comprises predicting which patients 65 years of age or older with LVH will progress to HFrEF comprising measuring NT-proBNP and high sensitive cardiac troponin T (hs cTnT) once and determining which subjects have values in the upper tertile (upper third) for their age and gender strata.

6. A method for predicting whether a human patient 65 years of age or older with left ventricular hypertrophy (LVH) is at increased risk for developing heart failure with reduced ejection fraction (HFrEF), comprising obtaining the results of an assay that measures levels of NT-proBNP and cardiac troponin T in a specimen from the patient wherein an increased NT-proBNP and cardiac troponin T level compared to levels in a control indicate an increased risk for developing heart failure with reduced ejection fraction (HFrEF), wherein the method further comprises administering to the patient an effective amount of one or more ACE inhibitors, angiotensin receptor blockers, beta-blockers, and combinations thereof.

7. A method for predicting whether a human patient 65 years of age or older with left ventricular hypertrophy (LVH) is at greater risk for developing heart failure with reduced ejection fraction (HFrEF), comprising obtaining the results of an assay that monitors levels of NT-proBNP and cardiac troponin T in specimens from the patient at an initial time to obtain baseline levels and again at a later time, wherein increasing levels of NT-proBNP and cardiac troponin T over that time period indicate an increased risk for developing heart failure with reduced ejection fraction (HFrEF), wherein the method further comprises administering to the patient an effective amount of one or more ACE inhibitors, angiotensin receptor blockers, beta-blockers, and combinations thereof.

8. The method of claim 6, wherein the method comprises detecting an increase in NT-proBNP>25% from baseline to a final concentration of >190 pg/ml and/or an increase in cardiac troponin T>50% from baseline.

9. The method of claim 6, wherein if a patient has a cardiac troponin T value below 3 ng/L, a value of 2.99 ng/L is imputed as the baseline value.

10. The method of claim 7, wherein the LVH is determined by a method selected from the group consisting of echocardiography, magnetic resonance imaging and electrocardiography.

11. A method for diagnosing the risk of progressing from left ventricular dysfunction to heart failure with a reduced ejection fraction in a human patient 65 years of age or older, the method comprising i) contacting in vitro a portion of a blood sample from a subject with a ligand comprising specific binding affinity for the cardiac troponin T isoform (cTnT), ii) contacting in vitro a portion of the blood sample from the subject with a ligand comprising specific binding affinity for NT-proBNP, iii) calculating an amount of the cTnT and an amount of NT-proBNP based on said steps of contacting, and iv) providing a diagnosis of increased risk of progressing to heart failure with a reduced ejection fraction if the concentration of cTnT is greater than or equal to age- and gender-specific cut points and the concentration of NT-proBNP is greater than or equal to age- and gender-specific cutpoints as defined below:

|             | hs-cTnT (pg/mL) || NT-proBNP (pg/mL) ||
| Age         | Male  | Female | Male  | Female |
|-------------|-------|--------|-------|--------|
| 65-69       | 7.54  | 6.06   | 93.2  | 122.4  |
| 70-74       | 9.23  | 6.00   | 130.5 | 147.7  |
| 75-70       | 10.84 | 7.83   | 152.8 | 246.3  |
| 80 or older | 16.61 | 11.07  | 304.9 | 341.2  | wherein the method further comprises administering to the patient an effective amount of one or more ACE inhibitors, angiotensin receptor blockers, beta-blockers, and combinations thereof.

* * * * *